US012312406B2

(12) United States Patent
Guo et al.

(10) Patent No.: US 12,312,406 B2
(45) Date of Patent: May 27, 2025

(54) ANTI-B7-H3 ANTIBODY, PREPARATION METHOD THEREFOR, CONJUGATE AND APPLICATION THEREOF

(71) Applicant: SHANGHAI FUDAN-ZHANGJIANG BIO-PHARMACEUTICAL CO., LTD., Shanghai (CN)

(72) Inventors: Qingsong Guo, Shanghai (CN); Fang Wu, Shanghai (CN); Tong Yang, Shanghai (CN); Yijun Shen, Shanghai (CN)

(73) Assignee: SHANGHAI FUDAN-ZHANGJIANG BIO-PHARMACEUTICAL CO., LTD., Shanghai (CN)

( * ) Notice: Subject to any disclaimer, the term of this patent is extended or adjusted under 35 U.S.C. 154(b) by 1036 days.

(21) Appl. No.: 17/292,488

(22) PCT Filed: Nov. 8, 2019

(86) PCT No.: PCT/CN2019/116590
§ 371 (c)(1),
(2) Date: May 10, 2021

(87) PCT Pub. No.: WO2020/094120
PCT Pub. Date: May 14, 2020

(65) Prior Publication Data
US 2022/0017620 A1    Jan. 20, 2022

(30) Foreign Application Priority Data

Nov. 9, 2018  (CN) .......................... 201811333430.X
Jul. 18, 2019  (CN) .......................... 201910649470.3

(51) Int. Cl.
*A61P 35/00* (2006.01)
*A61K 47/68* (2017.01)
*C07K 16/28* (2006.01)

(52) U.S. Cl.
CPC .... *C07K 16/2827* (2013.01); *A61K 47/68031* (2023.08); *A61K 47/68033* (2023.08); *A61K 47/6817* (2017.08); *A61K 47/6851* (2017.08); *A61P 35/00* (2018.01); *C07K 2317/24* (2013.01); *C07K 2317/622* (2013.01); *C07K 2317/76* (2013.01); *C07K 2317/77* (2013.01); *C07K 2317/92* (2013.01)

(58) Field of Classification Search
CPC .............. A61P 35/00; A61K 47/68031; A61K 47/68033; A61K 47/6817; A61K 47/6851; C07K 16/2827; C07K 2317/24; C07K 2317/622; C07K 2317/76; C07K 2317/77; C07K 2317/92
See application file for complete search history.

(56) References Cited

U.S. PATENT DOCUMENTS

| 2005/0002935 | A1  | 1/2005 | Ling et al. |
| 2013/0078234 | A1  | 3/2013 | Takahashi et al. |
| 2014/0127225 | A1* | 5/2014 | Basi ............. C07K 16/18 |
| | | | 530/387.3 |
| 2016/0137713 | A1* | 5/2016 | Kim ............. C07K 16/283 |
| | | | 435/254.2 |

FOREIGN PATENT DOCUMENTS

| CN | 1809370 A | 7/2006 |
| CN | 101104639 A | 1/2008 |
| CN | 103687945 A | 3/2014 |
| CN | 112239502 A | 1/2019 |
| CN | 110305213 B | 10/2019 |
| WO | 2011109400 A2 | 9/2011 |

OTHER PUBLICATIONS

King et al. "transformants." A Dictionary of Genetics (8 ed). (2013) Oxford University Press. eISBN: 9780199376865. (Year: 2013).*
Doerner et al. FEBS Letters (2014) 588: 278-287 (Year: 2014).*
Bruggemann et al. Arch. Immunol. Ther. Exp. (2015) 63: 101-118) (Year: 2015).*
Lopes dos Santos et al. Brazilian Journal of Pharmaceutical Sciences (2018) 54(Special): e01007 (Year: 2018).*
Pirkalkhoran et al. Bioengineering (2023) 10: 122 (Year: 2023).*
Aug. 10, 2023 First Search Report issued in Chinese Patent Application No. 2019106494703.
Aug. 11, 2023 First Office Action issued in Chinese Patent Application No. 2019106494703.
First Office Action issued in Chinese Patent Application No. 201811333430X, mailed Apr. 13, 2022.
Sep. 8, 2022 Second Office Action issued in Chinese Patent Application No. 201811333430X.
Jan. 23, 2020 International Search Report issued in International Patent Application No. PCT/CN2019/116590.

(Continued)

*Primary Examiner* — Brad Duffy
*Assistant Examiner* — Elizabeth A Shupe
(74) *Attorney, Agent, or Firm* — Pilloff Passino & Cosenza LLP; Rachel Pilloff; Sean Passino

(57) ABSTRACT

An anti-B7-H3 antibody, a preparation method therefor, a conjugate and an application thereof. The anti-B7-H3 antibody comprises a complementarity determining region: one or more of heavy chain CDR1, heavy chain CDR2, and heavy chain CDR3, and/or one or more of light chain CDR1, light chain CDR2, and light chain CDR3. A sequence of the complementarity determining region is as described in the specification. The anti-B7-H3 antibody is a fully human antibody, has a unique antigen binding epitope, and can specifically bind B7-H3 antigen on tumor cells. Moreover, the antibody can rapidly internalize into cells after binding to tumor cells, and can be used for ADC drug development to obtain better anti-tumor activity and efficacy to achieve the purpose of treating cancers.

28 Claims, 6 Drawing Sheets
Specification includes a Sequence Listing.

(56) References Cited

OTHER PUBLICATIONS

Jan. 23, 2020 Written Opinion of the International Searching Authority issued in International Patent Application No. PCT/CN2019/116590.

Zhang G. B et al., "Characterization and application of two novel monoclonal antibodies against 2IgB7-H3: expression analysis of 2IgB7-H3 on dendritic cells and tumor cells", Tissue Antigens., vol. 66, pp. 83-92, 2005-12-31.

Shi Zhengpeng et al., "Identification and characterization of monoclonal antibody Y4F11 against human B7-H3", Chin I Cell Mol Immunol, vol. 32, pp. 1402-1406, 2016.

Akkiko Nagase-Zembutsu, et al., Development of DS-5573a: a novel afucosylated mAb directed at B7-H3 with potent antitumor activity, Cancer Sci, May 2016, vol. 107, No. 5, p. 674-681 doi: 10.1111/cas. 12915. Epub Apr. 26, 2016.

\* cited by examiner

SEQUENCE LISTING

<160> NUMBER OF SEQ ID NOS: 101

<210> SEQ ID NO 1

```
<211> LENGTH: 534
<212> TYPE: PRT
<213> ORGANISM: Homo sapiens

<400> SEQUENCE: 1

Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
            20                  25                  30

Val Pro Glu Asp Pro Val Val Ala Leu Val Gly Thr Asp Ala Thr Leu
        35                  40                  45

Cys Cys Ser Phe Ser Pro Glu Pro Gly Phe Ser Leu Ala Gln Leu Asn
    50                  55                  60

Leu Ile Trp Gln Leu Thr Asp Thr Lys Gln Leu Val His Ser Phe Ala
65                  70                  75                  80

Glu Gly Gln Asp Gln Gly Ser Ala Tyr Ala Asn Arg Thr Ala Leu Phe
                85                  90                  95

Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
        115                 120                 125

Phe Gly Ser Ala Ala Val Ser Leu Gln Val Ala Ala Pro Tyr Ser Lys
    130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Gln Gly Tyr Pro Glu Ala Glu Val
                165                 170                 175

Phe Trp Gln Asp Gly Gln Gly Val Pro Leu Thr Gly Asn Val Thr Thr
            180                 185                 190

Ser Gln Met Ala Asn Glu Gln Gly Leu Phe Asp Val His Ser Ile Leu
        195                 200                 205

Arg Val Val Leu Gly Ala Asn Gly Thr Tyr Ser Cys Leu Val Arg Asn
    210                 215                 220

Pro Val Leu Gln Gln Asp Ala His Ser Ser Val Thr Ile Thr Pro Gln
225                 230                 235                 240

Arg Ser Pro Thr Gly Ala Val Glu Val Gln Val Pro Glu Asp Pro Val
                245                 250                 255

Val Ala Leu Val Gly Thr Asp Ala Thr Leu Arg Cys Ser Phe Ser Pro
            260                 265                 270

Glu Pro Gly Phe Ser Leu Ala Gln Leu Asn Leu Ile Trp Gln Leu Thr
        275                 280                 285

Asp Thr Lys Gln Leu Val His Ser Phe Thr Glu Gly Arg Asp Gln Gly
    290                 295                 300

Ser Ala Tyr Ala Asn Arg Thr Ala Leu Phe Pro Asp Leu Leu Ala Gln
305                 310                 315                 320

Gly Asn Ala Ser Leu Arg Leu Gln Arg Val Arg Val Ala Asp Glu Gly
                325                 330                 335

Ser Phe Thr Cys Phe Val Ser Ile Arg Asp Phe Gly Ser Ala Ala Val
            340                 345                 350

Ser Leu Gln Val Ala Ala Pro Tyr Ser Lys Pro Ser Met Thr Leu Glu
        355                 360                 365

Pro Asn Lys Asp Leu Arg Pro Gly Asp Thr Val Thr Ile Thr Cys Ser
    370                 375                 380

Ser Tyr Arg Gly Tyr Pro Glu Ala Glu Val Phe Trp Gln Asp Gly Gln
```

-continued

```
                385                 390                 395                 400
Gly Val Pro Leu Thr Gly Asn Val Thr Thr Ser Gln Met Ala Asn Glu
                    405                 410                 415

Gln Gly Leu Phe Asp Val His Ser Val Leu Arg Val Leu Gly Ala
                420                 425                 430

Asn Gly Thr Tyr Ser Cys Leu Val Arg Asn Pro Val Leu Gln Gln Asp
                    435                 440                 445

Ala His Gly Ser Val Thr Ile Thr Gly Gln Pro Met Thr Phe Pro Pro
                450                 455                 460

Glu Ala Leu Trp Val Thr Val Gly Leu Ser Val Cys Leu Ile Ala Leu
465                 470                 475                 480

Leu Val Ala Leu Ala Phe Val Cys Trp Arg Lys Ile Lys Gln Ser Cys
                485                 490                 495

Glu Glu Glu Asn Ala Gly Ala Glu Asp Gln Asp Gly Glu Gly Glu Gly
                    500                 505                 510

Ser Lys Thr Ala Leu Gln Pro Leu Lys His Ser Asp Ser Lys Glu Asp
                515                 520                 525

Asp Gly Gln Glu Ile Ala
            530

<210> SEQ ID NO 2
<211> LENGTH: 316
<212> TYPE: PRT
<213> ORGANISM: Homo sapiens

<400> SEQUENCE: 2

Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
                20                  25                  30

Val Pro Glu Asp Pro Val Val Ala Leu Val Gly Thr Asp Ala Thr Leu
            35                  40                  45

Cys Cys Ser Phe Ser Pro Glu Pro Gly Phe Ser Leu Ala Gln Leu Asn
    50                  55                  60

Leu Ile Trp Gln Leu Thr Asp Thr Lys Gln Leu Val His Ser Phe Ala
65                  70                  75                  80

Glu Gly Gln Asp Gln Gly Ser Ala Tyr Ala Asn Arg Thr Ala Leu Phe
                85                  90                  95

Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
        115                 120                 125

Phe Gly Ser Ala Ala Val Ser Leu Gln Val Ala Ala Pro Tyr Ser Lys
    130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Arg Gly Tyr Pro Glu Ala Glu Val
                165                 170                 175

Phe Trp Gln Asp Gly Gln Gly Val Pro Leu Thr Gly Asn Val Thr Thr
            180                 185                 190

Ser Gln Met Ala Asn Glu Gln Gly Leu Phe Asp Val His Ser Val Leu
        195                 200                 205

Arg Val Val Leu Gly Ala Asn Gly Thr Tyr Ser Cys Leu Val Arg Asn
    210                 215                 220
```

```
Pro Val Leu Gln Gln Asp Ala His Gly Ser Val Thr Ile Thr Gly Gln
225                 230                 235                 240

Pro Met Thr Phe Pro Pro Glu Ala Leu Trp Val Thr Val Gly Leu Ser
            245                 250                 255

Val Cys Leu Ile Ala Leu Leu Val Ala Leu Ala Phe Val Cys Trp Arg
                260                 265                 270

Lys Ile Lys Gln Ser Cys Glu Glu Asn Ala Gly Ala Glu Asp Gln
            275                 280                 285

Asp Gly Glu Gly Glu Gly Ser Lys Thr Ala Leu Gln Pro Leu Lys His
290                 295                 300

Ser Asp Ser Lys Glu Asp Asp Gly Gln Glu Ile Ala
305                 310                 315
```

<210> SEQ ID NO 3
<211> LENGTH: 316
<212> TYPE: PRT
<213> ORGANISM: Murine

<400> SEQUENCE: 3

```
Met Leu Arg Gly Trp Gly Gly Pro Ser Val Gly Val Cys Val Arg Thr
1               5                   10                  15

Ala Leu Gly Val Leu Cys Leu Cys Leu Thr Gly Ala Val Glu Val Gln
                20                  25                  30

Val Ser Glu Asp Pro Val Ala Leu Val Asp Thr Asp Ala Thr Leu
        35                  40                  45

Arg Cys Ser Phe Ser Pro Glu Pro Gly Phe Ser Leu Ala Gln Leu Asn
        50                  55                  60

Leu Ile Trp Gln Leu Thr Asp Thr Lys Gln Leu Val His Ser Phe Thr
65                  70                  75                  80

Glu Gly Arg Asp Gln Gly Ser Ala Tyr Ser Asn Arg Thr Ala Leu Phe
                85                  90                  95

Pro Asp Leu Leu Val Gln Gly Asn Ala Ser Leu Arg Leu Gln Arg Val
            100                 105                 110

Arg Val Thr Asp Glu Gly Ser Tyr Thr Cys Phe Val Ser Ile Gln Asp
            115                 120                 125

Phe Asp Ser Ala Ala Val Ser Leu Gln Val Ala Ala Pro Tyr Ser Lys
130                 135                 140

Pro Ser Met Thr Leu Glu Pro Asn Lys Asp Leu Arg Pro Gly Asn Met
145                 150                 155                 160

Val Thr Ile Thr Cys Ser Ser Tyr Gln Gly Tyr Pro Glu Ala Glu Val
                165                 170                 175

Phe Trp Lys Asp Gly Gln Gly Val Pro Leu Thr Gly Asn Val Thr Thr
            180                 185                 190

Ser Gln Met Ala Asn Glu Arg Gly Leu Phe Asp Val His Ser Val Leu
            195                 200                 205

Arg Val Val Leu Gly Ala Asn Gly Thr Tyr Ser Cys Leu Val Arg Asn
            210                 215                 220

Pro Val Leu Gln Gln Asp Ala His Gly Ser Val Thr Ile Thr Gly Gln
225                 230                 235                 240

Pro Leu Thr Phe Pro Pro Glu Ala Leu Trp Val Thr Val Gly Leu Ser
            245                 250                 255

Val Cys Leu Val Val Leu Leu Val Ala Leu Ala Phe Val Cys Trp Arg
                260                 265                 270

Lys Ile Lys Gln Ser Cys Glu Glu Glu Asn Ala Gly Ala Glu Asp Gln
            275                 280                 285
```

-continued

Asp Gly Asp Gly Glu Gly Ser Lys Thr Ala Leu Arg Pro Leu Lys Pro
    290                 295                 300

Ser Glu Asn Lys Glu Asp Gly Gln Glu Ile Ala
305                 310                 315

<210> SEQ ID NO 4
<211> LENGTH: 534
<212> TYPE: PRT
<213> ORGANISM: cynomolgus

<400> SEQUENCE: 4

Met Leu His Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
                20                  25                  30

Val Pro Glu Asp Pro Val Val Ala Leu Val Gly Thr Asp Ala Thr Leu
            35                  40                  45

Arg Cys Ser Phe Ser Pro Glu Pro Gly Phe Ser Leu Ala Gln Leu Asn
        50                  55                  60

Leu Ile Trp Gln Leu Thr Asp Thr Lys Gln Leu Val His Ser Phe Thr
65                  70                  75                  80

Glu Gly Arg Asp Gln Gly Ser Ala Tyr Ala Asn Arg Thr Ala Leu Phe
                85                  90                  95

Leu Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
        115                 120                 125

Phe Gly Ser Ala Ala Val Ser Leu Gln Val Ala Ala Pro Tyr Ser Lys
130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Arg Gly Tyr Pro Glu Ala Glu Val
                165                 170                 175

Phe Trp Gln Asp Gly Gln Gly Ala Pro Leu Thr Gly Asn Val Thr Thr
            180                 185                 190

Ser Gln Met Ala Asn Glu Gln Gly Leu Phe Asp Val His Ser Val Leu
        195                 200                 205

Arg Val Val Leu Gly Ala Asn Gly Thr Tyr Ser Cys Leu Val Arg Asn
    210                 215                 220

Pro Val Leu Gln Gln Asp Ala His Gly Ser Ile Thr Ile Thr Pro Gln
225                 230                 235                 240

Arg Ser Pro Thr Gly Ala Val Glu Val Gln Val Pro Glu Asp Pro Val
                245                 250                 255

Val Ala Leu Val Gly Thr Asp Ala Thr Leu Arg Cys Ser Phe Ser Pro
            260                 265                 270

Glu Pro Gly Phe Ser Leu Ala Gln Leu Asn Leu Ile Trp Gln Leu Thr
        275                 280                 285

Asp Thr Lys Gln Leu Val His Ser Phe Thr Glu Gly Arg Asp Gln Gly
    290                 295                 300

Ser Ala Tyr Ala Asn Arg Thr Ala Leu Phe Leu Asp Leu Leu Ala Gln
305                 310                 315                 320

Gly Asn Ala Ser Leu Arg Leu Gln Arg Val Arg Val Ala Asp Glu Gly
                325                 330                 335

Ser Phe Thr Cys Phe Val Ser Ile Arg Asp Phe Gly Ser Ala Ala Val

```
                    340             345             350
    Ser Leu Gln Val Ala Pro Tyr Ser Lys Pro Ser Met Thr Leu Glu
                355             360             365

Pro Asn Lys Asp Leu Arg Pro Gly Asp Thr Val Thr Ile Thr Cys Ser
            370             375             380

Ser Tyr Arg Gly Tyr Pro Glu Ala Glu Val Phe Trp Gln Asp Gly Gln
    385             390             395             400

Gly Ala Pro Leu Thr Gly Asn Val Thr Thr Ser Gln Met Ala Asn Glu
                    405             410             415

Gln Gly Leu Phe Asp Val His Ser Val Leu Arg Val Leu Gly Ala
                420             425             430

Asn Gly Thr Tyr Ser Cys Leu Val Arg Asn Pro Val Leu Gln Gln Asp
                435             440             445

Ala His Gly Ser Val Thr Ile Thr Gly Gln Pro Met Thr Phe Pro Pro
            450             455             460

Glu Ala Leu Trp Val Thr Val Gly Leu Ser Val Cys Leu Val Ala Leu
    465             470             475             480

Leu Val Ala Leu Ala Phe Val Cys Trp Arg Lys Ile Lys Gln Ser Cys
                485             490             495

Glu Glu Glu Asn Ala Gly Ala Glu Asp Gln Asp Gly Glu Gly Glu Gly
                500             505             510

Ser Lys Thr Ala Leu Gln Pro Leu Lys His Ser Asp Ser Lys Glu Asp
                515             520             525

Asp Gly Gln Glu Leu Ala
                530

<210> SEQ ID NO 5
<211> LENGTH: 253
<212> TYPE: PRT
<213> ORGANISM: Artificial Sequence
<220> FEATURE:
<223> OTHER INFORMATION: P1D1 scfv

<400> SEQUENCE: 5

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Ser Val Ala Gly Leu Asp Tyr Trp Gly Gln Gly Thr Leu
            100                 105                 110

Val Thr Val Ser Ser Gly Ser Ala Ser Ala Pro Thr Leu Gly Gln Gly
        115                 120                 125

Gly Gly Gly Gly Ser Gly Gly Gly Ser Gly Gly Gly Gly Ser Lys
    130                 135                 140

Thr Val Val Thr Gln Pro Pro Ser Ala Ser Gly Thr Pro Gly Gln Arg
145                 150                 155                 160

Val Thr Ile Ser Cys Ser Gly Ser Ser Ser Asn Ile Gly Ser Lys Tyr
```

```
                    165                 170                 175
Val Tyr Trp Tyr Gln Gln Leu Pro Gly Thr Ala Pro Arg Leu Leu Ile
            180                 185                 190

Tyr Arg Asn Asn Gln Arg Pro Ser Gly Val Pro Asp Arg Phe Ser Gly
        195                 200                 205

Ser Lys Ser Gly Thr Ser Ala Ser Leu Ala Ile Ser Gly Leu Arg Ser
    210                 215                 220

Glu Asp Glu Ser Asp Tyr Tyr Cys Ala Ser Trp Asp Arg Leu Lys
225                 230                 235                 240

Gly Tyr Ala Phe Gly Thr Gly Thr Lys Val Thr Val Leu
                245                 250

<210> SEQ ID NO 6
<211> LENGTH: 117
<212> TYPE: PRT
<213> ORGANISM: Artificial Sequence
<220> FEATURE:
<223> OTHER INFORMATION: VH

<400> SEQUENCE: 6

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Ser Val Ala Gly Leu Asp Tyr Trp Gly Gln Gly Thr Leu
            100                 105                 110

Val Thr Val Ser Ser
        115

<210> SEQ ID NO 7
<211> LENGTH: 8
<212> TYPE: PRT
<213> ORGANISM: Artificial Sequence
<220> FEATURE:
<223> OTHER INFORMATION: VH CDR

<400> SEQUENCE: 7

Gly Tyr Ser Phe Thr Ser Tyr Trp
1               5

<210> SEQ ID NO 8
<211> LENGTH: 8
<212> TYPE: PRT
<213> ORGANISM: Artificial Sequence
<220> FEATURE:
<223> OTHER INFORMATION: VH CDR2

<400> SEQUENCE: 8

Ile Tyr Pro Gly Asp Ser Asp Thr
1               5

<210> SEQ ID NO 9
```

```
<211> LENGTH: 10
<212> TYPE: PRT
<213> ORGANISM: Artificial Sequence
<220> FEATURE:
<223> OTHER INFORMATION: VH CDR3

<400> SEQUENCE: 9

Ala Arg Arg Ser Val Ala Gly Leu Asp Tyr
1               5                   10

<210> SEQ ID NO 10
<211> LENGTH: 110
<212> TYPE: PRT
<213> ORGANISM: Artificial Sequence
<220> FEATURE:
<223> OTHER INFORMATION: VL

<400> SEQUENCE: 10

Lys Thr Val Val Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Lys
            20                  25                  30

Tyr Val Tyr Trp Tyr Gln Gln Leu Pro Gly Thr Ala Pro Arg Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ser Asp Tyr Tyr Cys Ala Ser Trp Asp Asp Arg Leu
                85                  90                  95

Lys Gly Tyr Ala Phe Gly Thr Gly Thr Lys Val Thr Val Leu
            100                 105                 110

<210> SEQ ID NO 11
<211> LENGTH: 8
<212> TYPE: PRT
<213> ORGANISM: Artificial Sequence
<220> FEATURE:
<223> OTHER INFORMATION: VL CDR1

<400> SEQUENCE: 11

Ser Ser Asn Ile Gly Ser Lys Tyr
1               5

<210> SEQ ID NO 12
<211> LENGTH: 3
<212> TYPE: PRT
<213> ORGANISM: Artificial Sequence
<220> FEATURE:
<223> OTHER INFORMATION: VL CDR2

<400> SEQUENCE: 12

Arg Asn Asn
1

<210> SEQ ID NO 13
<211> LENGTH: 11
<212> TYPE: PRT
<213> ORGANISM: Artificial Sequence
<220> FEATURE:
<223> OTHER INFORMATION: VL CDR3

<400> SEQUENCE: 13

Ala Ser Trp Asp Asp Arg Leu Lys Gly Tyr Ala
```

<210> SEQ ID NO 14
<211> LENGTH: 256
<212> TYPE: PRT
<213> ORGANISM: Artificial Sequence
<220> FEATURE:
<223> OTHER INFORMATION: P2E5 scFv

<400> SEQUENCE: 14

Gln Val Thr Leu Lys Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ser
            20                  25                  30

Tyr Met Thr Trp Val Arg Gln Ala Pro Gly Met Gly Leu Glu Trp Val
        35                  40                  45

Ala Ser Met Lys Pro Asp Gly Ser Val Lys His Tyr Val Asp Ser Val
    50                  55                  60

Lys Gly Arg Phe Thr Ile Ser Arg Asp Asn Thr Lys Asn Ser Leu Asp
65                  70                  75                  80

Leu Gln Met Asn Ser Leu Arg Ala Glu Asp Thr Ala Val Tyr Tyr Cys
                85                  90                  95

Ser Ser Tyr Asp Thr Arg Trp Gly Trp Phe Asp Pro Trp Gly Glu Gly
            100                 105                 110

Thr Leu Val Thr Val Ser Ser Gly Ser Ala Ser Ala Pro Thr Leu Gly
        115                 120                 125

Gln Gly Gly Gly Gly Ser Gly Gly Gly Ser Gly Gly Gly
    130                 135                 140

Ser Gln Thr Val Val Thr Gln Glu Pro Ser Phe Ser Val Ser Pro Gly
145                 150                 155                 160

Gly Thr Val Thr Leu Thr Cys Gly Leu Asn Ser Gly Ser Val Ser Thr
                165                 170                 175

Ser Tyr Phe Pro Ser Trp Tyr Gln Gln Thr Pro Gly Gln Ala Pro Arg
            180                 185                 190

Thr Leu Ile Tyr Asn Thr Asn Thr Arg Ser Ser Gly Val Pro Asp Arg
        195                 200                 205

Phe Ser Gly Ser Ile Leu Gly Asn Lys Ala Ala Leu Thr Ile Thr Gly
    210                 215                 220

Ala Gln Ala Asp Asp Glu Ser Asp Tyr Tyr Cys Leu Leu Tyr Met Asp
225                 230                 235                 240

Ser Gly Pro His Trp Val Phe Gly Gly Gly Thr Lys Leu Thr Val Leu
                245                 250                 255

<210> SEQ ID NO 15
<211> LENGTH: 119
<212> TYPE: PRT
<213> ORGANISM: Artificial Sequence
<220> FEATURE:
<223> OTHER INFORMATION: VH

<400> SEQUENCE: 15

Gln Val Thr Leu Lys Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ser
            20                  25                  30

Tyr Met Thr Trp Val Arg Gln Ala Pro Gly Met Gly Leu Glu Trp Val
        35                  40                  45

```
Ala Ser Met Lys Pro Asp Gly Ser Val Lys His Tyr Val Asp Ser Val
    50                  55                  60

Lys Gly Arg Phe Thr Ile Ser Arg Asp Asn Thr Lys Asn Ser Leu Asp
65                  70                  75                  80

Leu Gln Met Asn Ser Leu Arg Ala Glu Asp Thr Ala Val Tyr Tyr Cys
                85                  90                  95

Ser Ser Tyr Asp Thr Arg Trp Gly Trp Phe Asp Pro Trp Gly Glu Gly
            100                 105                 110

Thr Leu Val Thr Val Ser Ser
        115
```

```
<210> SEQ ID NO 16
<211> LENGTH: 8
<212> TYPE: PRT
<213> ORGANISM: Artificial Sequence
<220> FEATURE:
<223> OTHER INFORMATION: VH CDR1

<400> SEQUENCE: 16

Gly Phe Thr Phe Ser Asn Ser Tyr
1               5
```

```
<210> SEQ ID NO 17
<211> LENGTH: 8
<212> TYPE: PRT
<213> ORGANISM: Artificial Sequence
<220> FEATURE:
<223> OTHER INFORMATION: VH CDR2

<400> SEQUENCE: 17

Met Lys Pro Asp Gly Ser Val Lys
1               5
```

```
<210> SEQ ID NO 18
<211> LENGTH: 12
<212> TYPE: PRT
<213> ORGANISM: Artificial Sequence
<220> FEATURE:
<223> OTHER INFORMATION: VH CDR3

<400> SEQUENCE: 18

Ser Ser Tyr Asp Thr Arg Trp Gly Trp Phe Asp Pro
1               5                   10
```

```
<210> SEQ ID NO 19
<211> LENGTH: 111
<212> TYPE: PRT
<213> ORGANISM: Artificial Sequence
<220> FEATURE:
<223> OTHER INFORMATION: VL

<400> SEQUENCE: 19

Gln Thr Val Val Thr Gln Glu Pro Ser Phe Ser Val Ser Pro Gly Gly
1               5                   10                  15

Thr Val Thr Leu Thr Cys Gly Leu Asn Ser Gly Ser Val Ser Thr Ser
            20                  25                  30

Tyr Phe Pro Ser Trp Tyr Gln Gln Thr Pro Gly Gln Ala Pro Arg Thr
        35                  40                  45

Leu Ile Tyr Asn Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80
```

Gln Ala Asp Asp Glu Ser Asp Tyr Tyr Cys Leu Leu Tyr Met Asp Ser
            85                  90                  95

Gly Pro His Trp Val Phe Gly Gly Gly Thr Lys Leu Thr Val Leu
            100                 105                 110

<210> SEQ ID NO 20
<211> LENGTH: 9
<212> TYPE: PRT
<213> ORGANISM: Artificial Sequence
<220> FEATURE:
<223> OTHER INFORMATION: VL CDR1

<400> SEQUENCE: 20

Ser Gly Ser Val Ser Thr Ser Tyr Phe
1               5

<210> SEQ ID NO 21
<211> LENGTH: 3
<212> TYPE: PRT
<213> ORGANISM: Artificial Sequence
<220> FEATURE:
<223> OTHER INFORMATION: VL CDR2

<400> SEQUENCE: 21

Asn Thr Asn
1

<210> SEQ ID NO 22
<211> LENGTH: 11
<212> TYPE: PRT
<213> ORGANISM: Artificial Sequence
<220> FEATURE:
<223> OTHER INFORMATION: VL CDR3

<400> SEQUENCE: 22

Leu Leu Tyr Met Asp Ser Gly Pro His Trp Val
1               5                   10

<210> SEQ ID NO 23
<211> LENGTH: 254
<212> TYPE: PRT
<213> ORGANISM: Artificial Sequence
<220> FEATURE:
<223> OTHER INFORMATION: P1E11 scFv

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Ala Arg Gly Gly Asp Tyr Trp Gly Gln Gly Thr Leu Val Thr
            100                 105                 110

Val Ser Ser Gly Ser Ala Ser Ala Pro Thr Leu Gly Gln Gly Gly Gly
        115                 120                 125

```
Gly Gly Ser Gly Gly Gly Ser Gly Gly Gly Ser Glu Ile Val
        130             135             140
Leu Thr Gln Ser Pro Leu Ser Leu Pro Val Thr Leu Gly Gln Pro Ala
145                 150                 155                 160
Ser Ile Ser Cys Arg Ser Gln Ser Leu Val His Ser Asp Gly Asn
                165                 170                 175
Thr Tyr Leu Asn Trp Phe Gln Arg Pro Gly Gln Ser Pro Arg Arg
            180                 185                 190
Leu Ile Tyr Lys Val Ser Asn Arg Asp Ser Gly Val Pro Asp Arg Phe
        195                 200                 205
Ser Gly Ser Gly Ser Gly Thr Asp Phe Thr Leu Lys Ile Ser Arg Val
210                 215                 220
Glu Ala Glu Asp Val Gly Phe Tyr Tyr Cys Met Gln Gly Thr His Trp
225                 230                 235                 240
Pro Pro Gly Thr Phe Gly Gln Gly Thr Lys Leu Glu Ile Lys
                245                 250
```

```
<210> SEQ ID NO 24
<211> LENGTH: 115
<212> TYPE: PRT
<213> ORGANISM: Artificial Sequence
<220> FEATURE:
<223> OTHER INFORMATION: VH

<400> SEQUENCE: 24

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Gly Tyr
            20                  25                  30
Tyr Met His Trp Val Arg Gln Ala Pro Gly Gln Gly Leu Glu Trp Met
        35                  40                  45
Gly Trp Ile Asn Pro Asn Ser Gly Gly Thr Asn Tyr Ala Gln Lys Phe
    50                  55                  60
Gln Gly Arg Val Thr Met Thr Arg Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Ala Arg Ala Arg Gly Gly Asp Tyr Trp Gly Gln Gly Thr Leu Val Thr
            100                 105                 110
Val Ser Ser
        115
```

```
<210> SEQ ID NO 25
<211> LENGTH: 8
<212> TYPE: PRT
<213> ORGANISM: Artificial Sequence
<220> FEATURE:
<223> OTHER INFORMATION: VH CDR1

<400> SEQUENCE: 25

Gly Tyr Thr Phe Thr Gly Tyr Tyr
1               5
```

```
<210> SEQ ID NO 26
<211> LENGTH: 8
<212> TYPE: PRT
<213> ORGANISM: Artificial Sequence
<220> FEATURE:
<223> OTHER INFORMATION: VH CDR2
```

```
<400> SEQUENCE: 26

Ile Asn Pro Asn Ser Gly Gly Thr
1               5

<210> SEQ ID NO 27
<211> LENGTH: 8
<212> TYPE: PRT
<213> ORGANISM: Artificial Sequence
<220> FEATURE:
<223> OTHER INFORMATION: VH CDR3

<400> SEQUENCE: 27

Ala Arg Ala Arg Gly Gly Asp Tyr
1               5

<210> SEQ ID NO 28
<211> LENGTH: 113
<212> TYPE: PRT
<213> ORGANISM: Artificial Sequence
<220> FEATURE:
<223> OTHER INFORMATION: VL

<400> SEQUENCE: 28

Glu Ile Val Leu Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Gly
                85                  90                  95

Thr His Trp Pro Pro Gly Thr Phe Gly Gln Gly Thr Lys Leu Glu Ile
            100                 105                 110

Lys

<210> SEQ ID NO 29
<211> LENGTH: 11
<212> TYPE: PRT
<213> ORGANISM: Artificial Sequence
<220> FEATURE:
<223> OTHER INFORMATION: VL CDR1

<400> SEQUENCE: 29

Gln Ser Leu Val His Ser Asp Gly Asn Thr Tyr
1               5                   10

<210> SEQ ID NO 30
<211> LENGTH: 3
<212> TYPE: PRT
<213> ORGANISM: Artificial Sequence
<220> FEATURE:
<223> OTHER INFORMATION: VL CDR2

<400> SEQUENCE: 30

Lys Val Ser
1

<210> SEQ ID NO 31
```

```
<211> LENGTH: 10
<212> TYPE: PRT
<213> ORGANISM: Artificial Sequence
<220> FEATURE:
<223> OTHER INFORMATION: VL CDR3

<400> SEQUENCE: 31

Met Gln Gly Thr His Trp Pro Pro Gly Thr
1               5                   10

<210> SEQ ID NO 32
<211> LENGTH: 256
<212> TYPE: PRT
<213> ORGANISM: Artificial Sequence
<220> FEATURE:
<223> OTHER INFORMATION: P1G2 scFv

<400> SEQUENCE: 32

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Val Asn Tyr Tyr Asp Ser Ser Gly Tyr Tyr Ser Asp Tyr Trp Gly
            100                 105                 110

Gln Gly Thr Leu Val Thr Val Ser Ser Gly Ser Ala Ser Ala Pro Thr
        115                 120                 125

Leu Gly Gln Gly Gly Gly Gly Ser Gly Gly Gly Gly Ser Gly Gly Gly
    130                 135                 140

Gly Gly Ser Ser Tyr Glu Leu Thr Gln Pro Pro Ser Ala Ser Gly Ser
145                 150                 155                 160

Pro Gly Gln Ser Val Thr Ile Ser Cys Thr Gly Thr Ser Ser Asp Val
                165                 170                 175

Gly Gly Tyr Asn Tyr Val Ser Trp Tyr Gln Gln His Pro Gly Lys Ala
            180                 185                 190

Pro Arg Leu Met Ile Tyr Gly Val Ser Gln Arg Pro Ser Gly Val Pro
        195                 200                 205

Asp Arg Phe Ser Gly Ser Lys Ser Gly Asn Thr Ala Ser Leu Thr Val
    210                 215                 220

Ser Gly Leu Gln Ala Glu Asp Glu Ala Asp Tyr Tyr Cys Ser Ser Tyr
225                 230                 235                 240

Ala Asn Asn Asn Tyr Val Phe Gly Thr Gly Thr Lys Val Thr Val Leu
                245                 250                 255

<210> SEQ ID NO 33
<211> LENGTH: 121
<212> TYPE: PRT
<213> ORGANISM: Artificial Sequence
<220> FEATURE:
<223> OTHER INFORMATION: VH

<400> SEQUENCE: 33
```

-continued

Gln Val Gln Leu Gln Gln Ser Gly Ala Glu Val Lys Lys Pro Gly Ser
1               5                   10                  15

Ser Val Lys Val Ser Cys Lys Ala Ser Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Val Asn Tyr Tyr Asp Ser Ser Gly Tyr Tyr Ser Asp Tyr Trp Gly
            100                 105                 110

Gln Gly Thr Leu Val Thr Val Ser Ser
            115                 120

<210> SEQ ID NO 34
<211> LENGTH: 8
<212> TYPE: PRT
<213> ORGANISM: Artificial Sequence
<220> FEATURE:
<223> OTHER INFORMATION: VH CDR1

<400> SEQUENCE: 34

Gly Gly Thr Phe Ser Ser Tyr Ala
1               5

<210> SEQ ID NO 35
<211> LENGTH: 8
<212> TYPE: PRT
<213> ORGANISM: Artificial Sequence
<220> FEATURE:
<223> OTHER INFORMATION: VH CDR2

<400> SEQUENCE: 35

Ile Ile Pro Ile Leu Gly Ile Ala
1               5

<210> SEQ ID NO 36
<211> LENGTH: 14
<212> TYPE: PRT
<213> ORGANISM: Artificial Sequence
<220> FEATURE:
<223> OTHER INFORMATION: VH CDR3

<400> SEQUENCE: 36

Ala Val Asn Tyr Tyr Asp Ser Ser Gly Tyr Tyr Ser Asp Tyr
1               5                   10

<210> SEQ ID NO 37
<211> LENGTH: 109
<212> TYPE: PRT
<213> ORGANISM: Artificial Sequence
<220> FEATURE:
<223> OTHER INFORMATION: VL

<400> SEQUENCE: 37

Ser Tyr Glu Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

```
Asn Tyr Val Ser Trp Tyr Gln Gln His Pro Gly Lys Ala Pro Arg Leu
             35                  40                  45

Met Ile Tyr Gly Val Ser Gln Arg Pro Ser Gly Val Pro Asp Arg Phe
 50                  55                  60

Ser Gly Ser Lys Ser Gly Asn Thr Ala Ser Leu Thr Val Ser Gly Leu
 65                  70                  75                  80

Gln Ala Glu Asp Glu Ala Asp Tyr Tyr Cys Ser Ser Tyr Ala Asn Asn
                 85                  90                  95

Asn Tyr Val Phe Gly Thr Gly Thr Lys Val Thr Val Leu
            100                 105
```

```
<210> SEQ ID NO 38
<211> LENGTH: 9
<212> TYPE: PRT
<213> ORGANISM: Artificial Sequence
<220> FEATURE:
<223> OTHER INFORMATION: VL CDR1

<400> SEQUENCE: 38

Ser Ser Asp Val Gly Gly Tyr Asn Tyr
1               5

<210> SEQ ID NO 39
<211> LENGTH: 3
<212> TYPE: PRT
<213> ORGANISM: Artificial Sequence
<220> FEATURE:
<223> OTHER INFORMATION: VL CDR2

<400> SEQUENCE: 39

Gly Val Ser
1

<210> SEQ ID NO 40
<211> LENGTH: 9
<212> TYPE: PRT
<213> ORGANISM: Artificial Sequence
<220> FEATURE:
<223> OTHER INFORMATION: VL CDR3

<400> SEQUENCE: 40

Ser Ser Tyr Ala Asn Asn Asn Tyr Val
1               5

<210> SEQ ID NO 41
<211> LENGTH: 253
<212> TYPE: PRT
<213> ORGANISM: Artificial Sequence
<220> FEATURE:
<223> OTHER INFORMATION: P3B09 scFv

<400> SEQUENCE: 41

Gln Ile Gln Leu Val Gln Ser Gly Ala Glu Val Lys Lys Pro Gly Glu
1               5                  10                  15

Ser Leu Lys Ile Ser Cys Lys Gly Ser Gly Tyr Ser Phe Thr Ser Tyr
             20                  25                  30

Trp Ile Gly Trp Val Arg Gln Met Pro Gly Lys Gly Leu Glu Trp Met
             35                  40                  45

Gly Ile Ile Tyr Pro Gly Asp Ser Asp Thr Arg Tyr Ser Pro Ser Phe
 50                  55                  60

Gln Gly Gln Val Thr Ile Ser Ala Asp Lys Ser Ile Ser Thr Ala Tyr
 65                  70                  75                  80
```

-continued

```
Leu Gln Trp Ser Ser Leu Lys Ala Ser Asp Thr Ala Met Tyr Tyr Cys
                85                  90                  95

Ala Arg Arg Thr Pro Arg Gly Met Asp Val Trp Gly Gln Gly Thr Thr
            100                 105                 110

Val Thr Val Ser Ser Gly Ser Ala Ser Ala Pro Thr Leu Gly Gln Gly
        115                 120                 125

Gly Gly Gly Gly Ser Gly Gly Gly Ser Gly Gly Gly Ser Gln
130                 135                 140

Ala Val Leu Thr Gln Pro Ser Ala Ser Gly Thr Pro Gly Gln Arg
145                 150                 155                 160

Val Thr Ile Ser Cys Ser Gly Ser Ser Asn Ile Gly Ser Asn Tyr
            165                 170                 175

Val Tyr Trp Tyr Gln Gln Leu Pro Gly Thr Ala Pro Lys Leu Leu Ile
        180                 185                 190

Tyr Arg Asn Asn Gln Arg Pro Ser Gly Val Pro Asp Arg Phe Ser Gly
            195                 200                 205

Ser Lys Ser Gly Thr Ser Ala Ser Leu Ala Ile Ser Gly Leu Arg Ser
        210                 215                 220

Glu Asp Glu Ala Asp Tyr Tyr Cys Ala Ala Trp Asp Ser Leu Ser
225                 230                 235                 240

Gly Trp Val Phe Gly Gly Gly Thr Lys Leu Thr Val Leu
            245                 250
```

<210> SEQ ID NO 42
<211> LENGTH: 117
<212> TYPE: PRT
<213> ORGANISM: Artificial Sequence
<220> FEATURE:
<223> OTHER INFORMATION: VH

<400> SEQUENCE: 42

```
Gln Ile Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Thr Pro Arg Gly Met Asp Val Trp Gly Gln Gly Thr Thr
            100                 105                 110

Val Thr Val Ser Ser
        115
```

<210> SEQ ID NO 43
<211> LENGTH: 10
<212> TYPE: PRT
<213> ORGANISM: Artificial Sequence
<220> FEATURE:
<223> OTHER INFORMATION: VH CDR3

<400> SEQUENCE: 43

```
Ala Arg Arg Thr Pro Arg Gly Met Asp Val
1               5                   10
```

<210> SEQ ID NO 44
<211> LENGTH: 110
<212> TYPE: PRT
<213> ORGANISM: Artificial Sequence
<220> FEATURE:
<223> OTHER INFORMATION: VL

<400> SEQUENCE: 44

Gln Ala Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Trp Val Phe Gly Gly Gly Thr Lys Leu Thr Val Leu
            100                 105                 110

<210> SEQ ID NO 45
<211> LENGTH: 8
<212> TYPE: PRT
<213> ORGANISM: Artificial Sequence
<220> FEATURE:
<223> OTHER INFORMATION: VL CDR1

<400> SEQUENCE: 45

Ser Ser Asn Ile Gly Ser Asn Tyr
1               5

<210> SEQ ID NO 46
<211> LENGTH: 11
<212> TYPE: PRT
<213> ORGANISM: Artificial Sequence
<220> FEATURE:
<223> OTHER INFORMATION: VL CDR3

<400> SEQUENCE: 46

Ala Ala Trp Asp Asp Ser Leu Ser Gly Trp Val
1               5                   10

<210> SEQ ID NO 47
<211> LENGTH: 253
<212> TYPE: PRT
<213> ORGANISM: Artificial Sequence
<220> FEATURE:
<223> OTHER INFORMATION: P2E3 scFv

<400> SEQUENCE: 47

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Ser Arg Glu Gly Phe Asp Pro Trp Gly Gln Gly Thr Leu
            100                 105                 110

Val Thr Val Ser Ser Gly Ser Ala Ser Ala Pro Thr Leu Gly Gln Gly
        115                 120                 125

Gly Gly Gly Gly Ser Gly Gly Gly Ser Gly Gly Gly Ser Gln
130                 135                 140

Ala Val Leu Thr Gln Pro Ser Ala Ser Gly Thr Pro Gly Gln Arg
145                 150                 155                 160

Val Thr Met Ser Cys Ser Gly Ala Ala Ser Asn Ile Gly Lys Asn Phe
                165                 170                 175

Val Tyr Trp Tyr Gln Gln Leu Pro Gly Arg Ala Pro Arg Leu Leu Ile
            180                 185                 190

Ser Arg Asn Ile Gln Arg Pro Ser Glu Val Pro Asp Arg Phe Ser Gly
            195                 200                 205

Ser Lys Ser Gly Thr Ser Ala Ser Leu Ala Ile Ser Gly Leu Gln Ser
210                 215                 220

Glu Asp Glu Ala Asp Tyr Tyr Cys Ala Ala Trp Asp Ser Leu Asn
225                 230                 235                 240

Gly Phe Val Phe Gly Thr Gly Thr Ala Val Thr Val Leu
                245                 250

```
<210> SEQ ID NO 48
<211> LENGTH: 117
<212> TYPE: PRT
<213> ORGANISM: Artificial Sequence
<220> FEATURE:
<223> OTHER INFORMATION: VH

<400> SEQUENCE: 48
```

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Ser Arg Glu Gly Phe Asp Pro Trp Gly Gln Gly Thr Leu
            100                 105                 110

Val Thr Val Ser Ser
        115

```
<210> SEQ ID NO 49
<211> LENGTH: 10
<212> TYPE: PRT
<213> ORGANISM: Artificial Sequence
<220> FEATURE:
<223> OTHER INFORMATION: VH CDR3
```

```
<400> SEQUENCE: 49

Ala Arg Arg Ser Arg Glu Gly Phe Asp Pro
1               5                   10

<210> SEQ ID NO 50
<211> LENGTH: 110
<212> TYPE: PRT
<213> ORGANISM: Artificial Sequence
<220> FEATURE:
<223> OTHER INFORMATION: VL

<400> SEQUENCE: 50

Gln Ala Val Leu Thr Gln Pro Ser Ser Ala Ser Gly Thr Pro Gly Gln
1               5                   10                  15

Arg Val Thr Met Ser Cys Ser Gly Ala Ala Ser Asn Ile Gly Lys Asn
            20                  25                  30

Phe Val Tyr Trp Tyr Gln Gln Leu Pro Gly Arg Ala Pro Arg Leu Leu
        35                  40                  45

Ile Ser Arg Asn Ile Gln Arg Pro Ser Glu Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Phe Val Phe Gly Thr Gly Thr Ala Val Thr Val Leu
            100                 105                 110

<210> SEQ ID NO 51
<211> LENGTH: 8
<212> TYPE: PRT
<213> ORGANISM: Artificial Sequence
<220> FEATURE:
<223> OTHER INFORMATION: VL CDR1

<400> SEQUENCE: 51

Ala Ser Asn Ile Gly Lys Asn Phe
1               5

<210> SEQ ID NO 52
<211> LENGTH: 3
<212> TYPE: PRT
<213> ORGANISM: Artificial Sequence
<220> FEATURE:
<223> OTHER INFORMATION: VL CDR2

<400> SEQUENCE: 52

Arg Asn Ile
1

<210> SEQ ID NO 53
<211> LENGTH: 11
<212> TYPE: PRT
<213> ORGANISM: Artificial Sequence
<220> FEATURE:
<223> OTHER INFORMATION: VL CDR3

<400> SEQUENCE: 53

Ala Ala Trp Asp Asp Ser Leu Asn Gly Phe Val
1               5                   10

<210> SEQ ID NO 54
<211> LENGTH: 435
<212> TYPE: PRT
```

<213> ORGANISM: Artificial Sequence
<220> FEATURE:
<223> OTHER INFORMATION: B7-H3 4Ig with 435 amino acids

<400> SEQUENCE: 54

```
Gly Ala Leu Glu Val Gln Val Pro Glu Asp Pro Val Val Ala Leu Val
1               5                   10                  15

Gly Thr Asp Ala Thr Leu Cys Cys Ser Phe Ser Pro Glu Pro Gly Phe
            20                  25                  30

Ser Leu Ala Gln Leu Asn Leu Ile Trp Gln Leu Thr Asp Thr Lys Gln
        35                  40                  45

Leu Val His Ser Phe Ala Glu Gly Gln Asp Gln Gly Ser Ala Tyr Ala
    50                  55                  60

Asn Arg Thr Ala Leu Phe Pro Asp Leu Leu Ala Gln Gly Asn Ala Ser
65                  70                  75                  80

Leu Arg Leu Gln Arg Val Arg Val Ala Asp Glu Gly Ser Phe Thr Cys
                85                  90                  95

Phe Val Ser Ile Arg Asp Phe Gly Ser Ala Ala Val Ser Leu Gln Val
            100                 105                 110

Ala Ala Pro Tyr Ser Lys Pro Ser Met Thr Leu Glu Pro Asn Lys Asp
        115                 120                 125

Leu Arg Pro Gly Asp Thr Val Thr Ile Thr Cys Ser Ser Tyr Gln Gly
    130                 135                 140

Tyr Pro Glu Ala Glu Val Phe Trp Gln Asp Gly Gln Gly Val Pro Leu
145                 150                 155                 160

Thr Gly Asn Val Thr Thr Ser Gln Met Ala Asn Glu Gln Gly Leu Phe
                165                 170                 175

Asp Val His Ser Ile Leu Arg Val Val Leu Gly Ala Asn Gly Thr Tyr
            180                 185                 190

Ser Cys Leu Val Arg Asn Pro Val Leu Gln Gln Asp Ala His Ser Ser
        195                 200                 205

Val Thr Ile Thr Pro Gln Arg Ser Pro Thr Gly Ala Val Glu Val Gln
    210                 215                 220

Val Pro Glu Asp Pro Val Val Ala Leu Val Gly Thr Asp Ala Thr Leu
225                 230                 235                 240

Arg Cys Ser Phe Ser Pro Glu Pro Gly Phe Ser Leu Ala Gln Leu Asn
                245                 250                 255

Leu Ile Trp Gln Leu Thr Asp Thr Lys Gln Leu Val His Ser Phe Thr
            260                 265                 270

Glu Gly Arg Asp Gln Gly Ser Ala Tyr Ala Asn Arg Thr Ala Leu Phe
        275                 280                 285

Pro Asp Leu Leu Ala Gln Gly Asn Ala Ser Leu Arg Leu Gln Arg Val
    290                 295                 300

Arg Val Ala Asp Glu Gly Ser Phe Thr Cys Phe Val Ser Ile Arg Asp
305                 310                 315                 320

Phe Gly Ser Ala Ala Val Ser Leu Gln Val Ala Ala Pro Tyr Ser Lys
                325                 330                 335

Pro Ser Met Thr Leu Glu Pro Asn Lys Asp Leu Arg Pro Gly Asp Thr
            340                 345                 350

Val Thr Ile Thr Cys Ser Ser Tyr Arg Gly Tyr Pro Glu Ala Glu Val
        355                 360                 365

Phe Trp Gln Asp Gly Gln Gly Val Pro Leu Thr Gly Asn Val Thr Thr
    370                 375                 380

Ser Gln Met Ala Asn Glu Gln Gly Leu Phe Asp Val His Ser Val Leu
```

```
                385                 390                 395                 400
Arg Val Val Leu Gly Ala Asn Gly Thr Tyr Ser Cys Leu Val Arg Asn
                    405                 410                 415

Pro Val Leu Gln Gln Asp Ala His Gly Ser Val Thr Ile Thr Gly Gln
                    420                 425                 430

Pro Met Thr
        435

<210> SEQ ID NO 55
<211> LENGTH: 217
<212> TYPE: PRT
<213> ORGANISM: Artificial Sequence
<220> FEATURE:
<223> OTHER INFORMATION: B7-H3 2Ig with 217 amino acids

<400> SEQUENCE: 55

Leu Glu Val Gln Val Pro Glu Asp Pro Val Val Ala Leu Val Gly Thr
1               5                   10                  15

Asp Ala Thr Leu Cys Cys Ser Phe Ser Pro Glu Pro Gly Phe Ser Leu
                20                  25                  30

Ala Gln Leu Asn Leu Ile Trp Gln Leu Thr Asp Thr Lys Gln Leu Val
            35                  40                  45

His Ser Phe Ala Glu Gly Gln Asp Gln Gly Ser Ala Tyr Ala Asn Arg
    50                  55                  60

Thr Ala Leu Phe Pro Asp Leu Leu Ala Gln Gly Asn Ala Ser Leu Arg
65                  70                  75                  80

Leu Gln Arg Val Arg Val Ala Asp Glu Gly Ser Phe Thr Cys Phe Val
                85                  90                  95

Ser Ile Arg Asp Phe Gly Ser Ala Ala Val Ser Leu Gln Val Ala Ala
                100                 105                 110

Pro Tyr Ser Lys Pro Ser Met Thr Leu Glu Pro Asn Lys Asp Leu Arg
            115                 120                 125

Pro Gly Asp Thr Val Thr Ile Thr Cys Ser Ser Tyr Arg Gly Tyr Pro
    130                 135                 140

Glu Ala Glu Val Phe Trp Gln Asp Gly Gln Gly Val Pro Leu Thr Gly
145                 150                 155                 160

Asn Val Thr Thr Ser Gln Met Ala Asn Glu Gln Gly Leu Phe Asp Val
                165                 170                 175

His Ser Val Leu Arg Val Val Leu Gly Ala Asn Gly Thr Tyr Ser Cys
            180                 185                 190

Leu Val Arg Asn Pro Val Leu Gln Gln Asp Ala His Gly Ser Val Thr
    195                 200                 205

Ile Thr Gly Gln Pro Met Thr Phe Pro
    210                 215

<210> SEQ ID NO 56
<211> LENGTH: 102
<212> TYPE: PRT
<213> ORGANISM: Artificial Sequence
<220> FEATURE:
<223> OTHER INFORMATION: B7-H3 IgC domain with 102 amino acids

<400> SEQUENCE: 56

Pro Tyr Ser Lys Pro Ser Met Thr Leu Glu Pro Asn Lys Asp Leu Arg
1               5                   10                  15

Pro Gly Asp Thr Val Thr Ile Thr Cys Ser Ser Tyr Gln Gly Tyr Pro
                20                  25                  30
```

```
Glu Ala Glu Val Phe Trp Gln Asp Gly Gln Gly Val Pro Leu Thr Gly
            35                  40                  45

Asn Val Thr Thr Ser Gln Met Ala Asn Glu Gln Gly Leu Phe Asp Val
 50                  55                  60

His Ser Ile Leu Arg Val Val Leu Gly Ala Asn Gly Thr Tyr Ser Cys
 65                  70                  75                  80

Leu Val Arg Asn Pro Val Leu Gln Gln Asp Ala His Ser Ser Val Thr
                 85                  90                  95

Ile Thr Pro Gln Arg Ser
            100

<210> SEQ ID NO 57
<211> LENGTH: 101
<212> TYPE: PRT
<213> ORGANISM: Artificial Sequence
<220> FEATURE:
<223> OTHER INFORMATION: B7-H3 IgV domian with 101 amino acids

<400> SEQUENCE: 57

Glu Val Gln Val Pro Glu Asp Pro Val Val Ala Leu Val Gly Thr Asp
 1               5                  10                  15

Ala Thr Leu Cys Cys Ser Phe Ser Pro Glu Pro Gly Phe Ser Leu Ala
            20                  25                  30

Gln Leu Asn Leu Ile Trp Gln Leu Thr Asp Thr Lys Gln Leu Val His
        35                  40                  45

Ser Phe Ala Glu Gly Gln Asp Gln Gly Ser Ala Tyr Ala Asn Arg Thr
 50                  55                  60

Ala Leu Phe Pro Asp Leu Leu Ala Gln Gly Asn Ala Ser Leu Arg Leu
 65                  70                  75                  80

Gln Arg Val Arg Val Ala Asp Glu Gly Ser Phe Thr Cys Phe Val Ser
                85                  90                  95

Ile Arg Asp Phe Gly
            100

<210> SEQ ID NO 58
<211> LENGTH: 451
<212> TYPE: PRT
<213> ORGANISM: Artificial Sequence
<220> FEATURE:
<223> OTHER INFORMATION: Full-length heavy chain of P1G2

<400> SEQUENCE: 58

Gln Val Gln Leu Gln Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
 50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Val Asn Tyr Tyr Asp Ser Ser Gly Tyr Tyr Ser Asp Tyr Trp Gly
            100                 105                 110

Gln Gly Thr Leu Val Thr Val Ser Ser Ala Ser Thr Lys Gly Pro Ser
        115                 120                 125
```

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 59
<211> LENGTH: 215
<212> TYPE: PRT
<213> ORGANISM: Artificial Sequence
<220> FEATURE:
<223> OTHER INFORMATION: Full-length light chain of P1G2

<400> SEQUENCE: 59

Ser Tyr Glu Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Arg Leu
                35                  40                  45

Met Ile Tyr Gly Val Ser Gln Arg Pro Ser Gly Val Pro Asp Arg Phe
 50                  55                  60

Ser Gly Ser Lys Ser Gly Asn Thr Ala Ser Leu Thr Val Ser Gly Leu
 65                  70                  75                  80

Gln Ala Glu Asp Glu Ala Asp Tyr Tyr Cys Ser Ser Tyr Ala Asn Asn
                 85                  90                  95

Asn Tyr Val Phe Gly Thr Gly Thr Lys Val Thr Val Leu Gly Gln Pro
                100                 105                 110

Lys Ala Ala Pro Ser Val Thr Leu Phe Pro Pro Ser Ser Glu Glu Leu
                115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
                180                 185                 190

Ser Tyr Ser Cys Gln Val Thr His Glu Gly Ser Thr Val Glu Lys Thr
                195                 200                 205

Val Ala Pro Thr Glu Cys Ser
                210                 215

<210> SEQ ID NO 60
<211> LENGTH: 449
<212> TYPE: PRT
<213> ORGANISM: Artificial Sequence
<220> FEATURE:
<223> OTHER INFORMATION: Full-length heavy chain of P2E5

<400> SEQUENCE: 60

Gln Val Thr Leu Lys Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ser
                20                  25                  30

Tyr Met Thr Trp Val Arg Gln Ala Pro Gly Met Gly Leu Glu Trp Val
                35                  40                  45

Ala Ser Met Lys Pro Asp Gly Ser Val Lys His Tyr Val Asp Ser Val
 50                 55                  60

Lys Gly Arg Phe Thr Ile Ser Arg Asp Asn Thr Lys Asn Ser Leu Asp
 65                 70                  75                  80

Leu Gln Met Asn Ser Leu Arg Ala Glu Asp Thr Ala Val Tyr Tyr Cys
                 85                  90                  95

Ser Ser Tyr Asp Thr Arg Trp Gly Trp Phe Asp Pro Trp Gly Glu Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

```
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 61
<211> LENGTH: 217
<212> TYPE: PRT
<213> ORGANISM: Artificial Sequence
<220> FEATURE:
<223> OTHER INFORMATION: Full-length light chain of P2E5

<400> SEQUENCE: 61

Gln Thr Val Val Thr Gln Glu Pro Ser Phe Ser Val Ser Pro Gly Gly
1               5                   10                  15

Thr Val Thr Leu Thr Cys Gly Leu Asn Ser Gly Ser Val Ser Thr Ser
            20                  25                  30

Tyr Phe Pro Ser Trp Tyr Gln Gln Thr Pro Gly Gln Ala Pro Arg Thr
            35                  40                  45

Leu Ile Tyr Asn Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80
```

Gln Ala Asp Asp Glu Ser Asp Tyr Tyr Cys Leu Leu Tyr Met Asp Ser
                85                  90                  95

Gly Pro His Trp Val Phe Gly Gly Thr Lys Leu Thr Val Leu Gly
            100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
        130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
        210                 215

<210> SEQ ID NO 62
<211> LENGTH: 445
<212> TYPE: PRT
<213> ORGANISM: Artificial Sequence
<220> FEATURE:
<223> OTHER INFORMATION: Full-length heavy chain of P1E11

<400> SEQUENCE: 62

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ala Arg Gly Gly Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
        260                 265                 270

Phe Asn Trp Tyr Val Asp Gly Val Glu Val His Asn Ala Lys Thr Lys
    275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 63
<211> LENGTH: 220
<212> TYPE: PRT
<213> ORGANISM: Artificial Sequence
<220> FEATURE:
<223> OTHER INFORMATION: Full-length light chain of P1E11

<400> SEQUENCE: 63

Glu Ile Val Leu Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Gly
                85                  90                  95

Thr His Trp Pro Pro Gly Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

```
Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 64
<211> LENGTH: 447
<212> TYPE: PRT
<213> ORGANISM: Artificial Sequence
<220> FEATURE:
<223> OTHER INFORMATION: Full-length heavy chain of P1D1

<400> SEQUENCE: 64

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Ser Val Ala Gly Leu Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285
```

```
Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445

<210> SEQ ID NO 65
<211> LENGTH: 216
<212> TYPE: PRT
<213> ORGANISM: Artificial Sequence
<220> FEATURE:
<223> OTHER INFORMATION: Full-length light chain of P1D1

<400> SEQUENCE: 65

Lys Thr Val Val Thr Gln Pro Pro Ser Ala Ser Gly Thr Pro Gly Gln
1               5                   10                  15

Arg Val Thr Ile Ser Cys Ser Gly Ser Ser Asn Ile Gly Ser Lys
            20                  25                  30

Tyr Val Tyr Trp Tyr Gln Gln Leu Pro Gly Thr Ala Pro Arg Leu Leu
            35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ser Asp Tyr Tyr Cys Ala Ser Trp Asp Asp Arg Leu
                85                  90                  95

Lys Gly Tyr Ala Phe Gly Thr Gly Thr Lys Val Thr Val Leu Gly Gln
                100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
                180                 185                 190

Arg Ser Tyr Ser Cys Gln Val Thr His Glu Gly Ser Thr Val Glu Lys
            195                 200                 205
```

Thr Val Ala Pro Thr Glu Cys Ser
    210                 215

<210> SEQ ID NO 66
<211> LENGTH: 447
<212> TYPE: PRT
<213> ORGANISM: Artificial Sequence
<220> FEATURE:
<223> OTHER INFORMATION: Full-length heavy chain of P3B9

<400> SEQUENCE: 66

Gln Ile Gln Leu Val Gln Ser Gly Ala Glu Val Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Thr Pro Arg Gly Met Asp Val Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
          355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
              405                 410                 415

Trp Gln Gln Gly Asn Val Phe Ser Cys Ser Val Met His Glu Ala Leu
              420                 425                 430

His Asn His Tyr Thr Gln Lys Ser Leu Ser Leu Ser Pro Gly Lys
              435                 440                 445

<210> SEQ ID NO 67
<211> LENGTH: 216
<212> TYPE: PRT
<213> ORGANISM: Artificial Sequence
<220> FEATURE:
<223> OTHER INFORMATION: Full-length light chain of P3B9

<400> SEQUENCE: 67

Gln Ala Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
                35                  40                  45

Ile Tyr Arg Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
210                 215

<210> SEQ ID NO 68
<211> LENGTH: 447
<212> TYPE: PRT
<213> ORGANISM: Artificial Sequence
<220> FEATURE:
<223> OTHER INFORMATION: Full-length heavy chain of P2E3

<400> SEQUENCE: 68

```
Gln Val Gln Leu Val Gln Ser Gly Ala Glu Val Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
            50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
            85                  90                  95

Ala Arg Arg Ser Arg Glu Gly Phe Asp Pro Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
            210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Val Leu Asp Ser
385                 390                 395                 400

Asp Gly Ser Phe Phe Leu Tyr Ser Lys Leu Thr Val Asp Lys Ser Arg
            405                 410                 415
```

-continued

Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
        435                 440                 445

<210> SEQ ID NO 69
<211> LENGTH: 216
<212> TYPE: PRT
<213> ORGANISM: Artificial Sequence
<220> FEATURE:
<223> OTHER INFORMATION: Full-length light chain of P2E3

<400> SEQUENCE: 69

Gln Ala Val Leu Thr Gln Pro Ser Ser Ala Ser Gly Thr Pro Gly Gln
1               5                   10                  15
Arg Val Thr Met Ser Cys Ser Gly Ala Ala Ser Asn Ile Gly Lys Asn
            20                  25                  30
Phe Val Tyr Trp Tyr Gln Gln Leu Pro Gly Arg Ala Pro Arg Leu Leu
        35                  40                  45
Ile Ser Arg Asn Ile Gln Arg Pro Ser Glu Val Pro Asp Arg Phe Ser
    50                  55                  60
Gly Ser Lys Ser Gly Thr Ser Ala Ser Leu Ala Ile Ser Gly Leu Gln
65                  70                  75                  80
Ser Glu Asp Glu Ala Asp Tyr Tyr Cys Ala Ala Trp Asp Asp Ser Leu
                85                  90                  95
Asn Gly Phe Val Phe Gly Thr Gly Thr Ala Val Thr Val Leu Gly Gln
            100                 105                 110
Pro Lys Ala Ala Pro Ser Val Thr Leu Phe Pro Pro Ser Ser Glu Glu
        115                 120                 125
Leu Gln Ala Asn Lys Ala Thr Leu Val Cys Leu Ile Ser Asp Phe Tyr
    130                 135                 140
Pro Gly Ala Val Thr Val Ala Trp Lys Ala Asp Ser Ser Pro Val Lys
145                 150                 155                 160
Ala Gly Val Glu Thr Thr Thr Pro Ser Lys Gln Ser Asn Asn Lys Tyr
                165                 170                 175
Ala Ala Ser Ser Tyr Leu Ser Leu Thr Pro Glu Gln Trp Lys Ser His
            180                 185                 190
Arg Ser Tyr Ser Cys Gln Val Thr His Glu Gly Ser Thr Val Glu Lys
        195                 200                 205
Thr Val Ala Pro Thr Glu Cys Ser
    210                 215

<210> SEQ ID NO 70
<211> LENGTH: 256
<212> TYPE: PRT
<213> ORGANISM: Artificial Sequence
<220> FEATURE:
<223> OTHER INFORMATION: P3-H6 scFv

<400> SEQUENCE: 70

Gln Val Gln Leu Val Gln Ser Gly Ala Glu Val Lys Lys Pro Gly Glu
1               5                   10                  15
Ser Leu Lys Ile Ser Cys Lys Gly Ser Gly Tyr Ser Phe Ser Asn Tyr
            20                  25                  30
Trp Ile Gly Trp Val Arg Gln Met Pro Gly Lys Gly Leu Glu Trp Met
        35                  40                  45
Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Arg Gly Tyr Pro Thr Asn Tyr Met Asp Val Trp Gly Arg
            100                 105                 110

Gly Thr Thr Val Thr Val Ser Ser Gly Ser Ala Ser Ala Pro Thr Leu
            115                 120                 125

Gly Gln Gly Gly Gly Gly Ser Gly Gly Gly Ser Gly Gly Gly
130                 135                 140

Gly Ser Gln Ala Val Leu Thr Gln Pro Pro Ser Val Ser Gly Ala Pro
145                 150                 155                 160

Arg Gln Arg Val Thr Ile Ser Cys Ser Gly Ser Ser Ser Asn Ile Gly
            165                 170                 175

Asn Asn Ile Val Ser Trp Tyr Gln His Leu Pro Gly Lys Ala Pro Arg
            180                 185                 190

Leu Leu Ile Tyr Arg Glu Arg Gln Arg Pro Ser Gly Val Pro Asp Arg
            195                 200                 205

Phe Ser Gly Ser Lys Ser Gly Thr Ser Ala Ser Leu Ala Ile Ser Gly
210                 215                 220

Leu Arg Ser Glu Asp Glu Ala Asp Tyr Tyr Cys Ala Thr Trp Asp Asp
225                 230                 235                 240

Ser Leu Asn Ser Trp Val Phe Gly Gly Gly Thr Lys Leu Thr Val Leu
            245                 250                 255

<210> SEQ ID NO 71
<211> LENGTH: 120
<212> TYPE: PRT
<213> ORGANISM: Artificial Sequence
<220> FEATURE:
<223> OTHER INFORMATION: heavy chain variable region of P3-H6

<400> SEQUENCE: 71

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Arg Gly Tyr Pro Thr Asn Tyr Met Asp Val Trp Gly Arg
            100                 105                 110

Gly Thr Thr Val Thr Val Ser Ser
            115                 120

<210> SEQ ID NO 72
<211> LENGTH: 8
<212> TYPE: PRT
<213> ORGANISM: Artificial Sequence
<220> FEATURE:
<223> OTHER INFORMATION: Heavy chain CDR1 of P3-H6

<400> SEQUENCE: 72

Gly Tyr Ser Phe Ser Asn Tyr Trp
1               5

<210> SEQ ID NO 73
<211> LENGTH: 216
<212> TYPE: PRT
<213> ORGANISM: Artificial Sequence
<220> FEATURE:
<223> OTHER INFORMATION: Full-length light chain of P9A12

<400> SEQUENCE: 73

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ala Tyr
            20                  25                  30

Asn Tyr Val Thr Trp Tyr Gln Gln Tyr Pro Gly Lys Ala Pro Lys Leu
        35                  40                  45

Met Ile Tyr Asp Val Ser Glu Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Phe Thr Ser Ser
                85                  90                  95

Ile Ser Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 74
<211> LENGTH: 13
<212> TYPE: PRT
<213> ORGANISM: Artificial Sequence
<220> FEATURE:
<223> OTHER INFORMATION: Heavy chain CDR3 of P3-H6

<400> SEQUENCE: 74

Ala Arg Ser Arg Gly Tyr Pro Thr Asn Tyr Met Asp Val
1               5                   10

<210> SEQ ID NO 75
<211> LENGTH: 110
<212> TYPE: PRT
<213> ORGANISM: Artificial Sequence
<220> FEATURE:
<223> OTHER INFORMATION: light chain variable region of P3-H6

<400> SEQUENCE: 75

```
Gln Ala Val Leu Thr Gln Pro Pro Ser Val Ser Gly Ala Pro Arg Gln
1               5                   10                  15

Arg Val Thr Ile Ser Cys Ser Gly Ser Ser Asn Ile Gly Asn Asn
            20                  25                  30

Ile Val Ser Trp Tyr Gln His Leu Pro Gly Lys Ala Pro Arg Leu Leu
        35                  40                  45

Ile Tyr Arg Glu Arg Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Ser Leu
                85                  90                  95

Asn Ser Trp Val Phe Gly Gly Gly Thr Lys Leu Thr Val Leu
            100                 105                 110
```

<210> SEQ ID NO 76
<211> LENGTH: 8
<212> TYPE: PRT
<213> ORGANISM: Artificial Sequence
<220> FEATURE:
<223> OTHER INFORMATION: light chain CDR1 of P3-H6

<400> SEQUENCE: 76

```
Ser Ser Asn Ile Gly Asn Asn Ile
1               5
```

<210> SEQ ID NO 77
<211> LENGTH: 3
<212> TYPE: PRT
<213> ORGANISM: Artificial Sequence
<220> FEATURE:
<223> OTHER INFORMATION: light chain CDR2 of P3-H6

<400> SEQUENCE: 77

```
Arg Glu Arg
1
```

<210> SEQ ID NO 78
<211> LENGTH: 11
<212> TYPE: PRT
<213> ORGANISM: Artificial Sequence
<220> FEATURE:
<223> OTHER INFORMATION: light chain CDR3 of P3-H6

<400> SEQUENCE: 78

```
Ala Thr Trp Asp Asp Ser Leu Asn Ser Trp Val
1               5                   10
```

<210> SEQ ID NO 79
<211> LENGTH: 254
<212> TYPE: PRT
<213> ORGANISM: Artificial Sequence
<220> FEATURE:
<223> OTHER INFORMATION: P7F10 scFv

<400> SEQUENCE: 79

```
Gln Val Gln Leu Gln Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Ser Trp Val Arg Gln Ala Pro Gly Lys Gly Leu Glu Trp Val
        35                  40                  45
```

Ser Val Ile Ser Gly Ser Gly Gly Ser Thr Phe Tyr Ala Asp Ser Val
   50                  55                  60

Lys Gly Arg Phe Thr Ile Ser Arg Asp Asn Ser Lys Asn Thr Leu Tyr
 65                  70                  75                  80

Leu Gln Val Asn Ser Leu Arg Ala Glu Asp Thr Ala Val Tyr Tyr Cys
                 85                  90                  95

Ala Lys Asp Gly Arg Thr Leu Ser Gly Met Asp Val Trp Gly Gln Gly
                100                 105                 110

Thr Thr Val Thr Val Ser Ser Gly Ser Ala Ser Ala Pro Thr Leu Gly
            115                 120                 125

Gln Gly Gly Gly Gly Ser Gly Gly Gly Ser Gly Gly Gly
        130                 135                 140

Ser Gln Pro Val Leu Thr Gln Pro Ser Ala Ser Gly Thr Pro Gly
145                 150                 155                 160

Gln Arg Val Thr Ile Ser Cys Ser Gly Ser Ser Ser Asn Ile Gly Ser
                165                 170                 175

Asn Pro Val Asn Trp Tyr Gln Leu Pro Gly Thr Ala Pro Lys Leu
            180                 185                 190

Leu Ile Tyr Asn Asn Gln Arg Pro Ser Gly Val Pro Asp Arg Phe
        195                 200                 205

Ser Gly Ser Lys Ser Gly Thr Ser Gly Ser Leu Ala Ile Ser Gly Leu
210                 215                 220

Gln Ser Glu Asp Glu Ala His Tyr Tyr Cys Ala Ala Trp Asp Val Ser
225                 230                 235                 240

Leu Lys Glu Val Phe Gly Gly Thr Lys Val Thr Val Leu
                245                 250

<210> SEQ ID NO 80
<211> LENGTH: 119
<212> TYPE: PRT
<213> ORGANISM: Artificial Sequence
<220> FEATURE:
<223> OTHER INFORMATION: heavy chain variable region of P7F10

<400> SEQUENCE: 80

Gln Val Gln Leu Gln Gln Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Pro Met Ser Trp Val Arg Gln Ala Pro Gly Lys Gly Leu Glu Trp Val
             35                  40                  45

Ser Val Ile Ser Gly Ser Gly Gly Ser Thr Phe Tyr Ala Asp Ser Val
   50                  55                  60

Lys Gly Arg Phe Thr Ile Ser Arg Asp Asn Ser Lys Asn Thr Leu Tyr
 65                  70                  75                  80

Leu Gln Val Asn Ser Leu Arg Ala Glu Asp Thr Ala Val Tyr Tyr Cys
                 85                  90                  95

Ala Lys Asp Gly Arg Thr Leu Ser Gly Met Asp Val Trp Gly Gln Gly
                100                 105                 110

Thr Thr Val Thr Val Ser Ser
            115

<210> SEQ ID NO 81
<211> LENGTH: 8
<212> TYPE: PRT
<213> ORGANISM: Artificial Sequence

```
<220> FEATURE:
<223> OTHER INFORMATION: Heavy chain CDR1 of P7F10

<400> SEQUENCE: 81

Gly Phe Thr Phe Ser Ser Tyr Pro
1               5

<210> SEQ ID NO 82
<211> LENGTH: 8
<212> TYPE: PRT
<213> ORGANISM: Artificial Sequence
<220> FEATURE:
<223> OTHER INFORMATION: Heavy chain CDR2 of P7F10

<400> SEQUENCE: 82

Ile Ser Gly Ser Gly Gly Ser Thr
1               5

<210> SEQ ID NO 83
<211> LENGTH: 12
<212> TYPE: PRT
<213> ORGANISM: Artificial Sequence
<220> FEATURE:
<223> OTHER INFORMATION: Heavy chain CDR3 of P7F10

<400> SEQUENCE: 83

Ala Lys Asp Gly Arg Thr Leu Ser Gly Met Asp Val
1               5                   10

<210> SEQ ID NO 84
<211> LENGTH: 109
<212> TYPE: PRT
<213> ORGANISM: Artificial Sequence
<220> FEATURE:
<223> OTHER INFORMATION: light chain variable region of P7F10

<400> SEQUENCE: 84

Gln Pro Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
                20                  25                  30

Pro Val Asn Trp Tyr Gln Gln Leu Pro Gly Thr Ala Pro Lys Leu Leu
            35                  40                  45

Ile Tyr Asn Asn Asn Gln Arg Pro Ser Gly Val Pro Asp Arg Phe Ser
        50                  55                  60

Gly Ser Lys Ser Gly Thr Ser Gly Ser Leu Ala Ile Ser Gly Leu Gln
65                  70                  75                  80

Ser Glu Asp Glu Ala His Tyr Tyr Cys Ala Ala Trp Asp Val Ser Leu
                85                  90                  95

Lys Glu Val Phe Gly Gly Gly Thr Lys Val Thr Val Leu
            100                 105

<210> SEQ ID NO 85
<211> LENGTH: 8
<212> TYPE: PRT
<213> ORGANISM: Artificial Sequence
<220> FEATURE:
<223> OTHER INFORMATION: light chain CDR1 of P7F10

<400> SEQUENCE: 85

Ser Ser Asn Ile Gly Ser Asn Pro
1               5
```

```
<210> SEQ ID NO 86
<211> LENGTH: 3
<212> TYPE: PRT
<213> ORGANISM: Artificial Sequence
<220> FEATURE:
<223> OTHER INFORMATION: light chain CDR2 of P7F10

<400> SEQUENCE: 86

Asn Asn Asn
1

<210> SEQ ID NO 87
<211> LENGTH: 10
<212> TYPE: PRT
<213> ORGANISM: Artificial Sequence
<220> FEATURE:
<223> OTHER INFORMATION: light chain CDR3 of P7F10

<400> SEQUENCE: 87

Ala Ala Trp Asp Val Ser Leu Lys Glu Val
1               5                   10

<210> SEQ ID NO 88
<211> LENGTH: 254
<212> TYPE: PRT
<213> ORGANISM: Artificial Sequence
<220> FEATURE:
<223> OTHER INFORMATION: P9A12 scFv

<400> SEQUENCE: 88

Gln Val Thr Leu Lys Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Gly Ile Asp Ala Phe Asp Ile Trp Gly Gln Gly Thr
            100                 105                 110

Met Val Thr Val Ser Ser Gly Ser Ala Ser Ala Pro Thr Leu Gly Gln
        115                 120                 125

Gly Gly Gly Gly Gly Ser Gly Gly Gly Ser Gly Gly Gly Gly Ser
    130                 135                 140

Gln Ser Ala Leu Thr Gln Pro Ala Ser Val Ser Gly Ser Pro Gly Gln
145                 150                 155                 160

Ser Ile Thr Ile Ser Cys Thr Gly Thr Ser Ser Asp Val Gly Ala Tyr
                165                 170                 175

Asn Tyr Val Thr Trp Tyr Gln Gln Tyr Pro Gly Lys Ala Pro Lys Leu
            180                 185                 190

Met Ile Tyr Asp Val Ser Glu Arg Pro Ser Gly Val Ser Asn Arg Phe
        195                 200                 205

Ser Gly Ser Lys Ser Gly Asn Thr Ala Ser Leu Thr Ile Ser Gly Leu
    210                 215                 220

Gln Ala Glu Asp Glu Ala Asp Tyr Tyr Cys Ser Ser Phe Thr Ser Ser
225                 230                 235                 240
```

```
Ile Ser Trp Val Phe Gly Gly Thr Lys Leu Thr Val Leu
                245                 250
```

<210> SEQ ID NO 89
<211> LENGTH: 118
<212> TYPE: PRT
<213> ORGANISM: Artificial Sequence
<220> FEATURE:
<223> OTHER INFORMATION: heavy chain variable region of P9A12

<400> SEQUENCE: 89

```
Gln Val Thr Leu Lys Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Gly Ile Asp Ala Phe Asp Ile Trp Gly Gln Gly Thr
            100                 105                 110

Met Val Thr Val Ser Ser
        115
```

<210> SEQ ID NO 90
<211> LENGTH: 8
<212> TYPE: PRT
<213> ORGANISM: Artificial Sequence
<220> FEATURE:
<223> OTHER INFORMATION: Heavy chain CDR1 of P9A12

<400> SEQUENCE: 90

```
Gly Phe Thr Phe Ser Ser Tyr Ala
1               5
```

<210> SEQ ID NO 91
<211> LENGTH: 8
<212> TYPE: PRT
<213> ORGANISM: Artificial Sequence
<220> FEATURE:
<223> OTHER INFORMATION: Heavy chain CDR2 of P9A12

<400> SEQUENCE: 91

```
Ile Ser Gly Ser Gly Gly Ser Thr
1               5
```

<210> SEQ ID NO 92
<211> LENGTH: 11
<212> TYPE: PRT
<213> ORGANISM: Artificial Sequence
<220> FEATURE:
<223> OTHER INFORMATION: Heavy chain CDR3 of P9A12

<400> SEQUENCE: 92

```
Ala Arg Gly Ala Gly Ile Asp Ala Phe Asp Ile
1               5                   10
```

<210> SEQ ID NO 93

```
<211> LENGTH: 110
<212> TYPE: PRT
<213> ORGANISM: Artificial Sequence
<220> FEATURE:
<223> OTHER INFORMATION: light chain variable region of P9A12

<400> SEQUENCE: 93

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ala Tyr
            20                  25                  30

Asn Tyr Val Thr Trp Tyr Gln Gln Tyr Pro Gly Lys Ala Pro Lys Leu
        35                  40                  45

Met Ile Tyr Asp Val Ser Glu Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Phe Thr Ser Ser
                85                  90                  95

Ile Ser Trp Val Phe Gly Gly Gly Thr Lys Leu Thr Val Leu
            100                 105                 110

<210> SEQ ID NO 94
<211> LENGTH: 9
<212> TYPE: PRT
<213> ORGANISM: Artificial Sequence
<220> FEATURE:
<223> OTHER INFORMATION: light chain CDR1 of P9A12

<400> SEQUENCE: 94

Ser Ser Asp Val Gly Ala Tyr Asn Tyr
1               5

<210> SEQ ID NO 95
<211> LENGTH: 3
<212> TYPE: PRT
<213> ORGANISM: Artificial Sequence
<220> FEATURE:
<223> OTHER INFORMATION: light chain CDR2 of P9A12

<400> SEQUENCE: 95

Asp Val Ser
1

<210> SEQ ID NO 96
<211> LENGTH: 10
<212> TYPE: PRT
<213> ORGANISM: Artificial Sequence
<220> FEATURE:
<223> OTHER INFORMATION: light chain CDR3 of P9A12

<400> SEQUENCE: 96

Ser Ser Phe Thr Ser Ser Ile Ser Trp Val
1               5                   10

<210> SEQ ID NO 97
<211> LENGTH: 450
<212> TYPE: PRT
<213> ORGANISM: Artificial Sequence
<220> FEATURE:
<223> OTHER INFORMATION: Full-length heavy chain of P3H6

<400> SEQUENCE: 97

Gln Val Gln Leu Val Gln Ser Gly Ala Glu Val Lys Lys Pro Gly Glu
```

```
1               5                    10                   15
Ser Leu Lys Ile Ser Cys Lys Gly Ser Gly Tyr Ser Phe Ser Asn Tyr
            20                   25                  30
Trp Ile Gly Trp Val Arg Gln Met Pro Gly Lys Gly Leu Glu Trp Met
            35                   40                  45
Gly Ile Ile Tyr Pro Gly Asp Ser Asp Thr Arg Tyr Ser Pro Ser Phe
            50                   55                  60
Gln Gly Gln Val Thr Ile Ser Ala Asp Lys Ser Ile Ser Thr Ala Tyr
65                  70                   75                  80
Leu Gln Trp Ser Ser Leu Lys Ala Ser Asp Thr Ala Met Tyr Tyr Cys
            85                   90                  95
Ala Arg Ser Arg Gly Tyr Pro Thr Asn Tyr Met Asp Val Trp Gly Arg
            100                  105                 110
Gly Thr Thr Val Thr Val Ser Ser Ala Ser Thr Lys Gly Pro Ser Val
            115                  120                 125
Phe Pro Leu Ala Pro Ser Ser Lys Ser Thr Ser Gly Gly Thr Ala Ala
            130                  135                 140
Leu Gly Cys Leu Val Lys Asp Tyr Phe Pro Glu Pro Val Thr Val Ser
145                 150                  155                 160
Trp Asn Ser Gly Ala Leu Thr Ser Gly Val His Thr Phe Pro Ala Val
            165                  170                 175
Leu Gln Ser Ser Gly Leu Tyr Ser Leu Ser Ser Val Val Thr Val Pro
            180                  185                 190
Ser Ser Ser Leu Gly Thr Gln Thr Tyr Ile Cys Asn Val Asn His Lys
            195                  200                 205
Pro Ser Asn Thr Lys Val Asp Lys Lys Val Glu Pro Lys Ser Cys Asp
            210                  215                 220
Lys Thr His Thr Cys Pro Pro Cys Pro Ala Pro Glu Leu Leu Gly Gly
225                 230                  235                 240
Pro Ser Val Phe Leu Phe Pro Pro Lys Pro Lys Asp Thr Leu Met Ile
            245                  250                 255
Ser Arg Thr Pro Glu Val Thr Cys Val Val Val Asp Val Ser His Glu
            260                  265                 270
Asp Pro Glu Val Lys Phe Asn Trp Tyr Val Asp Gly Val Glu Val His
            275                  280                 285
Asn Ala Lys Thr Lys Pro Arg Glu Glu Gln Tyr Asn Ser Thr Tyr Arg
            290                  295                 300
Val Val Ser Val Leu Thr Val Leu His Gln Asp Trp Leu Asn Gly Lys
305                 310                  315                 320
Glu Tyr Lys Cys Lys Val Ser Asn Lys Ala Leu Pro Ala Pro Ile Glu
            325                  330                 335
Lys Thr Ile Ser Lys Ala Lys Gly Gln Pro Arg Glu Pro Gln Val Tyr
            340                  345                 350
Thr Leu Pro Pro Ser Arg Glu Glu Met Thr Lys Asn Gln Val Ser Leu
            355                  360                 365
Thr Cys Leu Val Lys Gly Phe Tyr Pro Ser Asp Ile Ala Val Glu Trp
            370                  375                 380
Glu Ser Asn Gly Gln Pro Glu Asn Asn Tyr Lys Thr Thr Pro Pro Val
385                 390                  395                 400
Leu Asp Ser Asp Gly Ser Phe Phe Leu Tyr Ser Lys Leu Thr Val Asp
            405                  410                 415
Lys Ser Arg Trp Gln Gln Gly Asn Val Phe Ser Cys Ser Val Met His
            420                  425                 430
```

-continued

Glu Ala Leu His Asn His Tyr Thr Gln Lys Ser Leu Ser Leu Ser Pro
            435                 440                 445

Gly Lys
    450

<210> SEQ ID NO 98
<211> LENGTH: 449
<212> TYPE: PRT
<213> ORGANISM: Artificial Sequence
<220> FEATURE:
<223> OTHER INFORMATION: Full-length heavy chain of P7F10

<400> SEQUENCE: 98

Gln Val Gln Leu Gln Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Ser Trp Val Arg Gln Ala Pro Gly Lys Gly Leu Glu Trp Val
        35                  40                  45

Ser Val Ile Ser Gly Ser Gly Gly Ser Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Val Asn Ser Leu Arg Ala Glu Asp Thr Ala Val Tyr Tyr Cys
                85                  90                  95

Ala Lys Asp Gly Arg Thr Leu Ser Gly Met Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

```
Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 99
<211> LENGTH: 448
<212> TYPE: PRT
<213> ORGANISM: Artificial Sequence
<220> FEATURE:
<223> OTHER INFORMATION: Full-length heavy chain of P9A12

<400> SEQUENCE: 99

Gln Val Thr Leu Lys Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Gly Ile Asp Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240
```

```
Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 100
<211> LENGTH: 216
<212> TYPE: PRT
<213> ORGANISM: Artificial Sequence
<220> FEATURE:
<223> OTHER INFORMATION: Full-length light chain of P3H6

<400> SEQUENCE: 100

Gln Ala Val Leu Thr Gln Pro Pro Ser Val Ser Gly Ala Pro Arg Gln
1               5                   10                  15

Arg Val Thr Ile Ser Cys Ser Gly Ser Ser Ser Asn Ile Gly Asn Asn
            20                  25                  30

Ile Val Ser Trp Tyr Gln His Leu Pro Gly Lys Ala Pro Arg Leu Leu
        35                  40                  45

Ile Tyr Arg Glu Arg Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Asp Ser Leu
                85                  90                  95

Asn Ser Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160
```

```
Ala Gly Val Glu Thr Thr Thr Pro Ser Lys Gln Ser Asn Asn Lys Tyr
                165             170                 175

Ala Ala Ser Ser Tyr Leu Ser Leu Thr Pro Glu Gln Trp Lys Ser His
            180             185                 190

Arg Ser Tyr Ser Cys Gln Val Thr His Glu Gly Ser Thr Val Glu Lys
        195             200                 205

Thr Val Ala Pro Thr Glu Cys Ser
    210             215

<210> SEQ ID NO 101
<211> LENGTH: 215
<212> TYPE: PRT
<213> ORGANISM: Artificial Sequence
<220> FEATURE:
<223> OTHER INFORMATION: Full-length light chain of P7F10

<400> SEQUENCE: 101

Gln Pro Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Pro Val Asn Trp Tyr Gln Gln Leu Pro Gly Thr Ala Pro Lys Leu Leu
            35                  40                  45

Ile Tyr Asn Asn Asn Gln Arg Pro Ser Gly Val Pro Asp Arg Phe Ser
    50                  55                  60

Gly Ser Lys Ser Gly Thr Ser Gly Ser Leu Ala Ile Ser Gly Leu Gln
65                  70                  75                  80

Ser Glu Asp Glu Ala His Tyr Tyr Cys Ala Ala Trp Asp Val Ser Leu
                85                  90                  95

Lys Glu Val Phe Gly Gly Gly Thr Lys Val Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210             215
```

ANTI-B7-H3 ANTIBODY, PREPARATION METHOD THEREFOR, CONJUGATE AND APPLICATION THEREOF

The present application claims the priority of CN201811333430X, filed on Nov. 9, 2018 and CN2019106494703, filed on Jul. 18, 2019. The contents of which are incorporated herein by reference in their entireties.

TECHNICAL FIELD

The present disclosure relates to the field of antibodies, and specifically relates to antibodies that specifically bind to mammalian B7-H3, especially human B7-H3, and preparation methods therefor, conjugates and applications thereof; in particular to fully human antibodies and fully human antibody drug conjugates for the treatment of cancer.

BACKGROUND

B7-H3, also known as CD276, was first reported in 2001 (Chapoval A I et al., Nat Immmunol 2001, 2(3):269-274). The protein is not considered as a butyrophilin and myelin oligodendrocyte glycoprotein because it lacks a heptad structure and a B30.2 domain, and it is identified as belonging to B7 family, a member of the immunoglobulin superfamily (Chapoval A I et al., Nat Immmunol 2001, 2(3):269-274). Different from other members of the family such as PD-L1, B7-H4, CD80, CD86, etc., B7-H3 exists in two different variants in the human body, namely 2IgB7-H3 and 4IgB7-H3. Among them, 4IgB7-H3 is the exon duplicate of 2IgB7-H3, which is mainly exist in the form of 4Ig B7-H3 in human (Sun M et al., The Journal of Immunology 2002, 168(12): 6294-6297; Ling V et al., Genomics 2003, 82(3): 365-377; Steinberger P et al., J IMMUNOL 2004, 172(4): 2352-2359), while only contains 2IgB7-H3 structure in mice (Sun M et al., The Journal of Immunology 2002, 168(12): 6294-6297). The results of the study show that natural mouse 2IgB7-H3 and human 4IgB7-H3 had similar functions without functional difference (Ling V et al., Genomics 2003, 82(3):365-377; Hofmeyer K A et al., Proc Natl Acad Sci USA 2008, 105(30):10277-10278.), and the crystal structure shows that the FG loop in the IgV region of the protein is an important epitope for B7-H3 to perform its functions (Vigdorovich V et al., Structure 2013, 21(5):707-717).

Although the mRNA levels of B7-H3 are widely expressed, for example, high levels of B7-H3 mRNA can be detected in many tissues and organs of human body, including heart, liver, placenta, prostate, testis, uterus, pancreas, small intestine, and colon. However, the protein expression level is relatively limited to resting fibroblasts, endothelial cells, osteoblasts, amniotic fluid stem cells and other non-immune cells, as well as the surface of induced antigen-presenting cells and NK cells (Hofmeyer K A, et al., Proc Natl Acad Sci USA 2008, 105(30): 10277-10278; Yi K H et al., Immunol Rev 2009, 229(1): 145-151; Picarda E et al., CLIN CANCER RES 2016, 22(14): 3425-3431). The B7-H3 protein level is low in normal healthy tissues such as liver, lung, bladder, testis, prostate, breast, placenta, lymphatic organs and other organs of normal humans, but B7-H3 protein is overexpressed in a large number of malignant tumors and is an antigen as a tumor marker. Studies have shown that B7-H3 can be highly expressed in many cancers such as prostate cancer, ovarian cancer, colorectal cancer, renal cell carcinoma, non-small cell lung cancer, pancreatic cancer, melanoma, gastric cancer, bladder cancer, malignant glioma and osteosarcoma, and especially in a variety of cancers, including head and neck cancer, kidney cancer, brain glioma and thyroid cancer (Roth T J et al., CANCER RES 2007, 67(16): 7893-7900; Zang X et al., MODERN PATHOL 2010, 23(8): 1104-1112; Ingebrigtsen V A et al., INT J CANCER 2012, 131(11): 2528-2536; Sun J et al., Cancer Immunology, Immunotherapy 2010, 59(8):1163-1171; Crispen P L et al., CLIN CANCER RES 2008, 14(16): 5150-5157; Zhang G et al., LUNG CANCER 2009, 66(2): 245-249; Yamato I et al., Br J Cancer 2009, 101(10):1709-1716; Tekle C et al., INT J CANCER 2012, 130(10):2282-2290; Katayama A, et al., INT J ONCOL 2011, 38(5):1219-1226; Wu C P et al., World J Gastroenterol 2006, 12(3): 457-459; Wu D et al., ONCOL LETT 2015, 9(3):1420-1424). B7-H3 is not only expressed on tumor cells, but also highly expressed on tumor neovascular endothelial cells, which is a very broad-spectrum antigen as a tumor marker. The high expression of B7-H3 protein can promote cancer progression, which is related to the poor prognosis and poor survival benefits of patients.

Early research results indicate that B7-H3 can stimulate the activation of T cells, promote the proliferation of CD4 and CD8 cells and the secretion of IFN-γ. However, with further research's, it has now been shown that B7-H3, as an immune checkpoint, mainly acts as a suppressor of T cells, which down-regulates the activity of T cells, and is a negative regulator of T cells. Studies by Woong-Kyung Suh and Durbaka V R Prasad have shown that murine B7-H3 protein can significantly inhibit the proliferation of CD4 and CD8 cells in a dose-dependent manner (Suh W et al., NAT IMMUNOL 2003, 4(9):899-906; Prasad D V R et al., The Journal of Immunology 2004, 173(4):2500-2506). The study by Judith Leitner et al. has similarly shown that both human 4Ig-B7-H3Ig and 2Ig-B7-H3Ig can inhibit the proliferation of T cells in vitro, as well as the secretion of relevant cytokines in CD4 and CD8 cells (IFN-γ, IL-2, IL-10, IL-13) (Leitner J et al., EUR J IMMUNOL 2009, 39(7): 1754-1764). Further analysis indicated that B7-H3 mediates the inhibition of T cells proliferation mainly by inhibiting the production of IL-2. In mice, antibodies that target and neutralize B7-H3 can significantly promote the progression of experimental autoimmune encephalomyelitis (EAE) as well as the proliferation of CD4 cells, which objectively shows that B7-H3 has the function of inhibiting T cells in vivo (Prasad D V R et al., The Journal of Immunology 2004, 173(4): 2500-2506). In Woong-Kyung Suh's study, B7-H3-deficient mice similarly shows earlier onset of experimental autoimmune encephalomyelitis (caused by Th1 cells) compared to wild-type mice under EAE conditions, indicating that B7-H3 mainly inhibits Th1 cells (Suh W et al., NAT IMMUNOL 2003, 4(9):899-906). Taking together, there has been debate about the function of B7-H3 on T cells, but the promotion of T cell function by B7-H3 has only seen in the research in mice, while the promotion of T cell function by human B7-H3 has not been reported yet. Although the receptors for B7-H3 have not been identified, the main point of view in the current academic community is that B7-H3 is a negative regulatory molecule for T cells.

Based on the fact that B7-H3 can inhibit the activity of T cell and thereby mediate tumor cells escape from immune surveillance, blocking the binding of B7-H3 to unknown receptors and thus mediating T cell activation as well as suppressing tumor cell activity is proven effective, for example, the available clinical results have showed that Enoblituzumab (US2018134790A1) has different degrees of remission for different tumors and has good therapeutic effects. However, there are still many patients with disease progression, so there remains a large of clinical unmet needs to develop monoclonal antibodies against B7-H3 alone. In addition, the aforementioned antibody was screened by hybridoma and then humanized Although the antibody screened from hybridomas have been humanized, it still contains mouse-derived sequences which has potential immunogenicity risk, and the available clinical results show that its anti-tumor effect needs further improvement.

In view of the high expression of B7-H3 in a variety of tumors, and its high antigen abundance in different tumors, it is a suitable target for the development of antibody-conjugated drugs.

CONTENT OF THE PRESENT INVENTION

The technical problem to be solved in the present disclosure is to provide an anti-B7-H3 antibody, preparation method therefor, conjugate and application thereof for overcoming the lack of anti-B7-H3 antibodies and the defects that most of the antibodies in the prior art contain murine antibody sequences. The whole-human phage library screening was used in the present disclosure, and the obtained antibody sequences are all fully human-derived, with low potential immunogenicity risk and certain clinical application safety. Moreover, the described antibodies have internalization function, which can be used for ADC drug development with better anti-tumor activity and efficacy in order to achieve the purpose for treating cancer.

The present disclosure solves the above-mentioned technical problems through the following technical solutions:

Provided is an anti-B7-H3 antibody comprising the following complementarity determining regions: one or more of heavy chain CDR1, heavy chain CDR2, and heavy chain CDR3, and/or one or more of light chain CDR1, light chain CDR2, and light chain CDR3; the heavy chain CDR1 has an amino acid sequence of SEQ ID NO: 7, 16, 25, 34, 72, 81 or 90; the heavy chain CDR2 has an amino acid sequence of SEQ ID NO: 8, 17, 26, 35, 82 or 91; the heavy chain CDR3 has an amino acid sequence of SEQ ID NO: 9, 18, 27, 36, 43, 49, 74, 83 or 92; the light chain CDR1 has an amino acid sequence of SEQ ID NO: 11, 20, 29, 38, 45, 51, 76, 85 or 94; the light chain CDR2 has an amino acid sequence of SEQ ID NO: 12, 21, 30, 39, 52, 77, 86 or 95; the light chain CDR3 has an amino acid sequence of SEQ ID NO: 13, 22, 31, 40, 46, 53, 78, 87, or 96.

Preferably, in the above-mentioned anti-B7-H3 antibody:
the heavy chain CDR1 has an amino acid sequence of SEQ ID NO: 7, the heavy chain CDR2 has an amino acid sequence of SEQ ID NO: 8, and the heavy chain CDR3 has an amino acid sequence of SEQ ID NO: 9;
Or, the heavy chain CDR1 has an amino acid sequence of SEQ ID NO: 16, the heavy chain CDR2 has an amino acid sequence of SEQ ID NO: 17, and the heavy chain CDR3 has an amino acid sequence of SEQ ID NO: 18;
Or, the heavy chain CDR1 has an amino acid sequence of SEQ ID NO: 25, the heavy chain CDR2 has an amino acid sequence of SEQ ID NO: 26, and the heavy chain CDR3 has an amino acid sequence of SEQ ID NO: 27;
Or, the heavy chain CDR1 has an amino acid sequence of SEQ ID NO: 34, the heavy chain CDR2 has an amino acid sequence of SEQ ID NO: 35, and the heavy chain CDR3 has an amino acid sequence of SEQ ID NO: 36;
Or, the heavy chain CDR1 has an amino acid sequence of SEQ ID NO: ID NO. 7, the heavy chain CDR2 has an amino acid sequence of SEQ ID NO: 8, and the heavy chain CDR3 has an amino acid sequence of SEQ ID NO: 43;
Or, the heavy chain CDR1 has an amino acid sequence of SEQ ID NO: 7, the heavy chain CDR2 has an amino acid sequence of SEQ ID NO: 8, and the heavy chain CDR3 has an amino acid sequence of SEQ ID NO: 49;
Or, the heavy chain CDR1 has an amino acid sequence of SEQ ID NO: 72, the heavy chain CDR2 has an amino acid sequence of SEQ ID NO: 8, and the heavy chain CDR3 has an amino acid sequence of SEQ ID NO: 74;
Or, the heavy chain CDR1 has an amino acid sequence of SEQ ID NO: 81, the heavy chain CDR2 has an amino acid sequence of SEQ ID NO: 82, and the heavy chain CDR3 has an amino acid sequence of SEQ ID NO: 83;
Or, the heavy chain CDR1 has an amino acid sequence of SEQ ID NO: 90, the heavy chain CDR2 has an amino acid sequence of SEQ ID NO: 91, and the heavy chain CDR3 has an amino acid sequence of SEQ ID NO: 92.

The light chain CDR1 has an amino acid sequence of SEQ ID NO: 11, the light chain CDR2 has an amino acid sequence of SEQ ID NO: 12, and the light chain CDR3 has an amino acid sequence of SEQ ID NO: 13;
Or, the light chain CDR1 has an amino acid sequence of SEQ ID NO: 20, the light chain CDR2 has an amino acid sequence of SEQ ID NO: 21, and the light chain CDR3 has an amino acid sequence of SEQ ID NO: 22;
Or, the light chain CDR1 has an amino acid sequence of SEQ ID NO: 29, the light chain CDR2 has an amino acid sequence of SEQ ID NO: 30, and the light chain CDR3 has an amino acid sequence of SEQ ID NO: 31;
Or, the light chain CDR1 has an amino acid sequence of SEQ ID NO: 38, the light chain CDR2 has an amino acid sequence of SEQ ID NO: 39, and the light chain CDR3 has an amino acid sequence of SEQ ID NO: 40;
Or, the light chain CDR1 has an amino acid sequence of SEQ ID NO: 45, the light chain CDR2 has an amino acid sequence of SEQ ID NO: 12, and the light chain CDR3 has an amino acid sequence of SEQ ID NO: 46;
Or, the light chain CDR1 has an amino acid sequence of SEQ ID NO: 51, the light chain CDR2 has an amino acid sequence of SEQ ID NO: 52, and the light chain CDR3 has an amino acid sequence of SEQ ID NO: 53;
Or, the light chain CDR1 has an amino acid sequence of SEQ ID NO: 76, the light chain CDR2 has an amino acid sequence of SEQ ID NO: 77, and the light chain CDR3 has an amino acid sequence of SEQ ID NO: 78;
Or, the light chain CDR1 has an amino acid sequence of SEQ ID NO: 85, the light chain CDR2 has an amino acid sequence of SEQ ID NO: 86, and the light chain CDR3 has an amino acid sequence of SEQ ID NO: 87;
Or, the light chain CDR1 has an amino acid sequence of SEQ ID NO: 94, the light chain CDR2 has an amino acid sequence of SEQ ID NO: 95, and the light chain CDR3 has an amino acid sequence of SEQ ID NO: 96.

More preferably, the anti-B7-H3 antibody comprises a heavy chain variable region (also referred to as VH domain) and/or a light chain variable region (also referred to as VL domain), or equivalents with one or more conserved amino acid substitutions and homologs thereof; the heavy chain variable region has an amino acid sequence of SEQ ID NO: 6, 15, 24, 33, 42, 48, 71, 80 or 89, or has an amino acid sequence having at least 90% homology with the amino acid sequence of SEQ ID NO: 6, 15, 24, 33, 42, 48, 71, 80 or 89; The light chain variable region has an amino acid sequence of SEQ ID NO: 10, 19, 28, 37, 44, 50, 75, 84 or 93, or has an amino acid sequence having at least 90% homology with the amino acid sequence of SEQ ID NO: 10, 19, 28, 37, 44, 50, 75, 84 or 93. The amino acid sequence "having at least 90% homology" in the present disclosure is obtained by inserting, deleting or substituting the amino acids shown in the aforementioned sequences, and the substitution may be: for example, analyzing the structures of the sequences by computer simulation, and analyzing the potential post-translational modifications (PTMs) that may exist, especially the PTMs in the CDR regions, including analyzing and substituting the aggregation sites of antibodies and asparagine deamidation sites (NG, NS, NH, etc.), aspartic acid isomerization (DG, DP) sensitive sites, N-glycosylation (N-{P}S/T) sensitive sites and oxidation sensitive sites.

The anti-B7-H3 antibody comprises or consists of a polypeptide having a VH domains comprising an amino acid sequence of any one of SEQ ID NO: 6, 15, 24, 33, 42, 48, 71, 80 and 89 and a VL domains comprising an amino acid sequence of any one of SEQ ID NO: 10, 19, 28, 37, 44, 50, 75, 84, and 93 to provide a VH/VL pairs indicating the antigen binding sites of the antibodies.

More preferably, the heavy chain variable region has an amino acid sequence of SEQ ID NO: 6, and the light chain variable region has an amino acid sequence of SEQ ID NO: 10;

Or, the heavy chain variable region has an amino acid sequence of SEQ ID NO: 15, and the light chain variable region has an amino acid sequence of SEQ ID NO: 19;

Or, the heavy chain variable region has an amino acid sequence of SEQ ID NO: 24, and the light chain variable region has an amino acid sequence of SEQ ID NO: 28;

Or, the heavy chain variable region has an amino acid sequence of SEQ ID NO: 33, and the light chain variable region has an amino acid sequence of SEQ ID NO: 37;

Or, the heavy chain variable region has an amino acid sequence of SEQ ID NO: 42, and the light chain variable region has an amino acid sequence of SEQ ID NO: 44;

Or, the heavy chain variable region has an amino acid sequence of SEQ ID NO: 48, and the light chain variable region has an amino acid sequence of SEQ ID NO: 50;

Or, the heavy chain variable region has an amino acid sequence of SEQ ID NO: 71, and the light chain variable region has an amino acid sequence of SEQ ID NO: 75;

Or, the heavy chain variable region has an amino acid sequence of SEQ ID NO: 80, and the light chain variable region has an amino acid sequence of SEQ ID NO: 84;

Or, the heavy chain variable region has an amino acid sequence of SEQ ID NO: 89, and the light chain variable region has an amino acid sequence of SEQ ID NO: 93.

More preferably, the anti-B7-H3 antibody further comprises a heavy chain constant region of an antibody and/or a light chain constant region of an antibody; the heavy chain constant region of antibody is preferably a heavy chain constant region of human or mouse antibody; and the light chain constant region of antibody is preferably a light chain constant region of human or mouse antibody; the light chain constant region of human antibody is preferably a kappa or lambda light chain constant region of human antibody; and the heavy chain constant region of human antibody is preferably a human IgG1, IgG2, IgG3 or IgG4.

In a preferably embodiment, the amino acid sequence of the heavy chain of the anti-B7-H3 antibody is set forth in SEQ ID NO: 58, 60, 62, 64, 66, 68, 97, 98 or 99, or has at least 90% homology with the amino acid sequence of SEQ ID NO: 58, 60, 62, 64, 66, 68, 97, 98 or 99; The amino acid sequence of the light chain of the anti-B7-H3 antibody is set forth in SEQ ID NO: 59, 61, 63, 65, 67, 69, 100, 101, or has at least 90% homology with the amino acid sequence of 59, 61, 63, 65, 67, 69, 100, 101 or 73; Preferably, the heavy chain of the anti-B7-H3 antibody has an amino acid sequence of SEQ ID NO: 58, and the light chain of the anti-B7-H3 antibody has an amino acid sequence of SEQ ID NO: 59; or the heavy chain of the anti-B7-H3 antibody has an amino acid sequence of SEQ ID NO: 60, and the light chain of the anti-B7-H3 antibody has an amino acid sequence of SEQ ID NO: 61; or the heavy chain of the anti-B7-H3 antibody has an amino acid sequence of SEQ ID NO: 62, and the light chain of the anti-B7-H3 antibody has an amino acid sequence of SEQ ID NO: 63; or the heavy chain of the anti-B7-H3 antibody has an amino acid sequence of SEQ ID NO: 64, and the light chain of the anti-B7-H3 antibody has an amino acid sequence of SEQ ID NO: 65; or the heavy chain of the anti-B7-H3 antibody has an amino acid sequence of SEQ ID NO: 66, and the light chain of the anti-B7-H3 antibody has an amino acid sequence of SEQ ID NO: 67; or the heavy chain of the anti-B7-H3 antibody has an amino acid sequence of SEQ ID NO: 68, and the light chain of the anti-B7-H3 antibody has an amino acid sequence of SEQ ID NO: 69; or the heavy chain of the anti-B7-H3 antibody has an amino acid sequence of SEQ ID NO: 97, and the light chain of the anti-B7-H3 antibody has an amino acid sequence of SEQ ID NO: 100; or the heavy chain of the anti-B7-H3 antibody has an amino acid sequence of SEQ ID NO: 98, and the light chain of the anti-B7-H3 antibody has an amino acid sequence of SEQ ID NO: 101; or the heavy chain of the anti-B7-H3 antibody has an amino acid sequence of SEQ ID NO: 99, and the light chain of the anti-B7-H3 antibody has an amino acid sequence of SEQ ID NO: 73.

The anti-B7-H3 antibody described in the present disclosure can be in the form of any of the following antibodies:
  (a) an intact immunoglobulin molecule;
  (b) a scFv;
  (c) a fusion protein containing scFv;
  (d) a Fab fragment;
  (e) a Fab' fragment;
  (f) a F(ab)$_2$;

In the anti-B7-H3 antibody of the present disclosure, the scFv preferably has an amino acid sequence of SEQ ID NO: 5, 14, 23, 32, 41, 47, 70, 79 or 88.

The anti-B7-H3 antibody described in the present disclosure can be a monoclonal antibody or a polyclonal antibody, and the monoclonal antibody is preferably a fully human monoclonal antibody.

The anti-B7-H3 antibody described in the present disclosure can be a superhumanized antibody or diabody.

The B7-H3 involved in the anti-B7-H3 antibody described in the present disclosure may be conventional B7-H3 in the art, such as soluble B7-H3, membrane form of B7-H3, etc., and the soluble B7-H3 is for example, human B7-H3 variant 1 with the sequence shown in SEQ ID NO: 1, human B7-H3 variant 2 with the sequence shown in SEQ ID NO: 2, B7-H3 expressed on human monocytes, mouse B7-H3 with the sequence shown in SEQ ID NO: 3, B7-H3 expressed on mouse monocytes, cynomolgus B7-H3 with the sequence shown in SEQ ID NO: 4, B7-H3 expressed on the cynomolgus monocytes, B7-H3 with the sequence shown in SEQ ID NO: 54, B7-H3 with the sequence shown in SEQ ID NO: 55, the IgC domain of B7-H3 with the sequence shown in SEQ ID NO: 56, or the IgV domain of B7-H3 with the sequence shown in SEQ ID NO: 57, etc. Preferably, the B7-H3 described in the present disclosure is B7-H3 endogenously expressed on the surface of cancer cells; more preferably, the anti-B7-H3 antibody is internalized upon binding to the B7-H3 endogenously expressed on the surface of cancer cells.

The anti-B7-H3 antibody described in the present disclosure has a dissociation constant (KD) of preferably $10^{-9}$M or less, more preferably $10^{-11}$M or less.

The present disclosure also provides antibody groups (including molecules comprising or consisting of antibody fragments or variants), wherein the group members correspond to one, two, three, four, five, or more different antibodies (e.g., intact antibody, Fab, F(ab)$_2$ fragment, scFv, etc.) of the present disclosure.

The anti-B7-H3 antibody described in the present disclosure is a B7-H3 antagonist, especially a human B7-H3 antagonist. A B7-H3 protein-specific antagonist (or referred to herein as a "B7-H3 specific antagonist") is a B7-H3 protein-specific binding molecule or protein that effectively inhibits the function of B7-H3, for example, it may contain a presently disclosed CDR domains or sets of heavy chain and/or light chain CDR domains and their equivalents with one or more conservative amino acid substitutions.

They are of great importance in the treatment of disorders associated with the function of B7-H3 or B7-H3 expression, including but not limited to prostate cancer, ovarian cancer, colorectal cancer, renal cell carcinoma, non-small cell lung cancer, pancreatic cancer, melanoma, gastric cancer, bladder cancer, malignant glioma and osteosarcoma and other related B7-H3 expressing tumors. B7-H3 specific antagonists are characterized by selective recognition and binding of B7-H3. The B7-H3 specific antagonist does not show significant binding to substances other than B7-H3, except in those special cases: the antagonist is supplemented with another specificity that is different from the B7-H3 specific binding portion. In a specific embodiment, the B7-H3 specific antagonist binds to human B7-H3 with a KD of $1.2\times10^{-6}$ or less. In a specific embodiment, the B7-H3 specific antagonist binds to human B7-H3 with a KD of $1\times10^{-7}$ or less. In another embodiment, the B7-H3 specific antagonist binds to human B7-H3 with a KD of $1\times10^{-8}$ or less. In other embodiments, the B7-H3 specific antagonist binds to human B7-H3 with a KD of $5\times10^{-9}$ or less, or $1\times10^{-9}$ or less. In other embodiments, the B7-H3 specific antagonist binds to human B7-H3 with a KD of $1\times10^{-10}$ or less, $1\times10^{-11}$ or less, or $1\times10^{-12}$ or less. In a specific embodiment, the B7-H3 specific antagonist does not bind to other proteins at the levels described above.

B7-H3 specific antagonists that specifically binding to B7-H3 can effectively internalize into cells. It has been repeatedly proved that the binding of B7-H3 specific antagonist can bring its coupled toxicant molecules into cells through internalization and cause apoptosis, while the specific activity that causes apoptosis is dose-dependent. Therefore, B7-H3 specific antagonists are of great importance for killing tumor cells. The B7-H3 specific antagonist of the present disclosure can also be used for various diagnostic purposes in detecting and quantifying B7-H3.

Those skilled in the art will understand that B7-H3 specific antagonist fragments that retain the ability to antagonize B7-H3 can be inserted into various frameworks. See, for example, U.S. Pat. No. 6,818,418 and the references therein, which has discussed various scaffolds used for displaying antibody loops that are previously selected based on antigen binding.

B7-H3 specific antagonists and fragments can be in the forms of various non-antibody-based scaffolds, including but not limited to high-affinity polymers (avimers) (Avidia); DARPins (Molecular Partners); Adnectins (Adnexus), Anticalins (Pieris) and Affibodies (Affibody). There have been many discussions on the use of alternative scaffolds for protein binding in many scientific literatures, see, for example, Binz & Plückthun, 2005 Curr. Opin. Biotech. 16: 1-11. Therefore, non-antibody-based scaffolds or antagonist molecules that specifically bind B7-H3 with specificity and selectivity for B7-H3, or that can be internalized upon binding, constitute an important embodiment of the present disclosure.

Also provided is a nucleic acid encoding the anti-B7-H3 antibody described herein.

Also provided is a recombinant expression vector comprising the nucleic acid described herein.

Also provided is a transformant comprising the recombinant expression vector described herein or having the presently disclosed nucleic acid integrated into its genome.

Also provided is a method for the preparation of an anti-B7-H3 antibody comprising the following steps: culturing the transformant described herein, and harvesting B7-H3 antibody from the culture.

Also provided is an immunoconjugate comprising the anti-B7-H3 antibody described herein; preferably, the immunoconjugate is an antibody-drug conjugate (ADC) or chimeric antigen receptor T cells (CAR-T); more preferably, the anti-B7-H3 antibody and cytotoxic agent are connected through a linker in the antibody-drug conjugate; the linker is preferably SMCC or VC-PAB, the cytotoxic agent is preferably MMAE or maytansine, and the drug-antibody ratio (DAR) of the anti-B7-H3 antibody to the maytansine is 3.2-4.0, such as 3.5.

Further provided is a pharmaceutical composition comprising the immunoconjugate described herein and a pharmaceutically acceptable carrier.

Further provided is use of the anti-B7-H3 antibody, or the immunoconjugate or the pharmaceutical composition described herein in the manufacture of a medicament for the treatment of a disease associated with abnormal expression of B7-H3; the disease associated with abnormal expression is preferably a tumor, the tumor is preferably a cancer, and the cancer is preferably lung cancer, breast cancer, prostate cancer, pancreatic cancer, colorectal cancer, melanoma, liver cancer, ovarian cancer, bladder cancer, stomach cancer, esophageal cancer, or kidney cancer.

Based on the common knowledge in the art, aforesaid preferred conditions can be combined arbitrarily to obtain the preferable embodiments of the present disclosure.

The reagents and raw materials used in the present disclosure are commercially available.

The advantage of the present invention is that the anti-B7-H3 antibody of the present disclosure is a fully human antibody screened by phage library and has unique antigen binding epitopes; the antibody can specifically bind to antigen B7-H3 expressed on tumor cells, and can be quickly internalized upon binding to tumor cells, which can be used for ADC drug development with better anti-tumor activity and efficacy in order to achieve the purpose for treating cancer.

DETAILED DESCRIPTION OF THE PREFERRED EMBODIMENT

Figure 1:
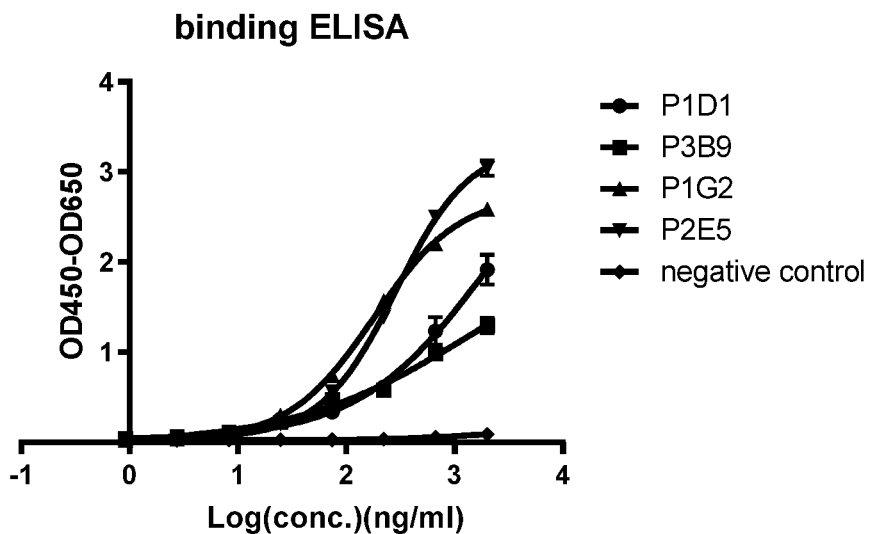
FIG. 1 shows the protein binding of different antibodies to B7-H3.

The term "B7-H3" as used herein is used in the same meaning as the B7-H3 protein, and also denotes B7-H3 variant 1 and/or B7-H3 variant 2.

The B7-H3 specific antagonist as defined herein selectively recognizes and specifically binds to B7-H3.

The term "selectively" or "specifically" as used herein refers to the fact that the disclosed antagonist does not show significant binding to substances other than B7-H3, except in those special cases where the antagonist is supplemented with another specificity that is different from the B7-H3 specific binding portion (for example, a bispecific or bifunctional molecule, wherein the molecule is designed to bind or perform two functions, at least one of which is specific for binding B7-H3).

KD refers to the dissociation constant obtained from the ratio of Kd (dissociation rate of specific binding molecule-target protein interaction) to Ka (binding rate of specific binding molecule-target protein interaction) (or Kd/Ka, expressed as molar concentration (M)). The KD value can be determined using methods that are well established in the art. A preferred method for determining the KD of a binding molecule is by using surface plasmon resonance, for example, a biosensor system such as the Biacore™ (GE Healthcare Life Sciences) system.

As used herein, "antibody molecule" or "antibody" refers to immunoglobulin molecule and immunologically active portion of immunoglobulin molecule, that is, a molecule containing an antigen binding site that immunospecifically binds to an antigen. Therefore, the term antibody encompasses not only intact antibody molecule, but also fragment of the antibody and variants (including derivatives) of the antibody and antibody fragment. The term antibody molecule in this disclosure includes, but is not limited to, single-chain Fv (scFv), Fab fragment, Fab' fragment, F(ab')$_2$, disulfide-linked Fv (sdFv), Fv, and an intact antibody or a full-length antibody. The term "single chain Fv" or "scFv" refers to a polypeptide comprising a VL domain of an antibody linked to a VH domain of an antibody. Antibodies that immunospecifically bind to B7-H3 can cross-react with other antigens. Preferably, antibodies that immunospecifically bind to B7-H3 do not cross-react with other antigens. Antibodies that immunospecifically bind to B7-H3 can be identified, for example, by immunoassays or other methods known to those skilled in the art. An "intact" antibody or a "full-length" antibody refers to a protein comprising two heavy chains (H) and two light chains (L), wherein the heavy chains and light chains are linked to each other by disulfide bonds, and the protein comprises: (1) a heavy chain comprising a variable region (herein abbreviated as "VH") and a heavy chain constant region comprising three domains CHL CH2, CH3; and (2) a light chain comprising a light chain variable region (abbreviated as "VL" herein) and a light chain constant region comprising one domain CL. The antibodies of the present disclosure include, but are not limited to, monoclonal, multi-specific, human or chimeric antibodies, single-chain antibodies, Fab fragments, F(ab') fragments, anti-idiotypic (anti-Id) antibodies (including, for example, the anti-Id antibodies of the present disclosure), and epitope binding fragments of any of the above antibodies. The immunoglobulin molecule of the present disclosure can be of any type (for example, IgG, IgE, IgM, IgD, IgA and IgY), class (for example, IgG1, IgG2, IgG3, IgG4, IgA1 and IgA2) or subclass of immunoglobulin. Preferably, the antibody of the present disclosure comprises or consists of a VH domain, a VH CDR, a VL domain, or a VL CDR having any amino acid sequence or a fragment or variant thereof described in Table 1.

The antibody of the present disclosure that "binds to a soluble B7-H3" is an antibody that binds to a soluble human B7-H3 protein with 435 amino acids (SEQ ID NO: 54), that is, 4Ig B7-H3 protein; and/or a soluble human B7-H3 with 217 amino acids (SEQ ID NO: 55), that is, 2Ig B7-H3 protein; and/or the IgC domain of a soluble human B7-H3 with 102 amino acids (SEQ ID NO: 56); and/or the IgV domain of a soluble human B7-H3 with 101 amino acids (SEQ ID NO: 57). In a specific embodiment of the present disclosure, the B7-H3 specific antagonist described herein binds to a soluble human B7-H3 protein with 435 amino acids, and preferably an antibody that simultaneously binds to a soluble human B7-H3 with 216 amino acids.

The antibody of the present disclosure that "binds to a membrane form of B7-H3" is an antibody that binds to a membrane B7-H3 protein. In a specific embodiment of the present disclosure, the antibody that "binds to the membrane form of B7-H3" described herein does not bind to the soluble B7-H3. Detection of binding to B7-H3 transfected CHO cells (as described herein) in ELISA is a way to detect the specificity of antibody binding to membrane form of B7-H3. Assays that can be used to detect the specificity of antibody binding to membrane form of B7-H3 include, but are not limited to, the binding to membrane expression B7-H3 as described in Example 5. The antibody of the present disclosure that "binds to a soluble B7-H3 and a membrane form of B7-H3" is an antibody that binds both the membrane form of B7-H3 and the soluble B7-H3.

The term "variant" refers to a polypeptide that has similar or identical functions with B7-H3 polypeptides, B7-H3 fragments, anti-B7-H3 antibodies or fragments thereof, but does not limited to comprise polypeptides similar or identical to the B7-H3 polypeptides, B7-H3 fragments, anti-B7-H3 antibody or fragments thereof, or the structure similar or identical to the B7-H3 polypeptides, B7-H3 fragments, anti-B7-H3 antibody or fragments thereof. A variant having a similar amino acid sequence is referred to as a polypeptide which conforms to at least one of the following: (a) a polypeptide comprising or consisting of an amino acid sequence having at least 30%, 35%, 40%, 45%, 50%, 55%, 60%, 65%, 70%, 75%, 80%, 85%, 90%, 95% or at least 99% homology with the amino acid sequence of B7-H3 polypeptides, B7-H3 fragments, anti-B7-H3 antibodies or fragments thereof (including VH domains, VHCDRs, VL domains, or VLCDRs comprising any of the amino acid sequences shown in Table 1); (b) a polypeptide comprising at least 5, 10, 15, 20, 25, 30, 40, 50, 60, 70, 80, 90, 100, 125, or at least 150 amino acid residues encoded by a nucleotide sequence whose complementary sequence hybridizes with the nucleotide sequences encoding a B7-H3 polypeptide, a B7-H3 fragment, an anti-B7-H3 antibody or fragments thereof (including a VH domain, a VHCDR, a VL domain, or a VLCDR comprising any of the amino acid sequences shown in Table 1) under strict hybridization conditions; (c) a polypeptide encoded by a nucleotide sequence having at least 30%, 35%, 40%, 45%, 50%, 55%, 60%, 65%, 70%, 75%, 80%, 85%, 90%, 95% or at least 99% homology with the nucleotide sequence encoding a B7-H3 polypeptide, a B7-H3 fragment, an anti-B7-H3 antibody or fragments thereof (including a VH domain, a VHCDR, a VL domain, or a VLCDR comprising any of the amino acid sequences shown in Table 1). A polypeptide having a similar structure to the B7-H3 polypeptide, B7-H3 fragment, anti-B7-H3 antibody or fragments thereof refers to a polypeptide that has a similar secondary, tertiary or quaternary structure to the B7-H3 polypeptide, B7-H3 fragment, anti-B7-H3 antibody or fragments thereof. The structure of the polypeptide can be determined by methods known to those skilled in the art, including but not limited to X-ray crystallization, nuclear magnetic resonance, and crystal electron microscopy.

As used herein, the percent homology between two amino acid sequences is equal to the percent identity between the two sequences. The percent identity between two sequences is a function of the number of identical positions shared by the sequences (i.e., % homology=number of identical positions/total number of positions×100), where the number of gaps and the length of each gap are considered and needs to be introduced for optimal alignment for the two sequences. Methods commonly known in the art can be used to compare sequences and determine the percent identity between sequences, for example, mathematical algorithms can be used to compare sequences and determine the percent identity. For example, the algorithm of Meyers and Miller, 1988 Comput. Appl. Biosci. 4:11-17 (integrated into ALIGN program (version 2.0)) can be used to determine the percent identity between amino acid sequences and/or nucleotide sequences. In addition, the GAP program (using its default parameters) in the GCG software package available online from Accelrys can be used to determine the percent identity between amino acid sequences or between nucleotide sequences. In one embodiment, two sequences are of equal length.

The term "epitope" refers to a portion of B7-H3 that has antigenicity or immunogenicity in an animal, preferably a mammal. The epitope with immunogenicity is a portion of B7-H3 which elicits an antibody response in an animal. The epitope with antigenicity is a portion of B7-H3 to which the antibody immunospecifically binds, which can be determined by methods known in the art, such as immunoassay methods described herein. The antigenic epitope is not necessarily immunogenic.

In one specific aspect, provided is an isolated B7-H3 specific antagonist that antagonize B7-H3. In one specific embodiment, the B7-H3 specific antagonist specifically binds to B7-H3 and blocks the binding to its unknown receptor. The B7-H3 specific antagonist of the present disclosure (e.g., the antibody molecule P1G2 or P2E5) binds to B7-H3 in a dose-dependent manner in repeated experiments. Therefore, in one specific embodiment, the present disclosure includes a B7-H3 specific antagonist. In one more specific embodiment, the present disclosure includes an antibody molecule that contains a heavy chain and/or light chain variable region, as well as their equivalents (characterized by having one or more conserved amino acid substitutions) or homologs. The term "domain" or "region" as used herein simply refers to portion of an antibody molecule in which there will be a sequence or fragment that will reside or is currently at issue.

Those skilled in the art will understand that conservative amino acid substitution is a substitution of an amino acid residue with an amino acid residue that result in similar or better (compared to the intended purpose) functional properties and/or chemical properties. For example, conservative amino acid substitution is often where amino acid residues are substituted by amino acid residues with similar side chains. Families of amino acid residues with similar side chains has been defined in the art.

These families include amino acids with the following side chains: basic side chains (for example, lysine, arginine, histidine), acidic side chains (for example, aspartic acid, glutamic acid), uncharged polar side chains (e.g., glycine, asparagine, glutamine, serine, threonine, tyrosine, cysteine, tryptophan), non-polar side chains (e.g., alanine, valine, leucine, isoleucine, proline, phenylalanine, methionine), β-branched side chains (for example, threonine, valine, isoleucine) and aromatic side chains (for example, tyrosine, phenylalanine, tryptophan, histidine). Such modifications are not intended to significantly reduce or change the binding or functional characteristics of B7-H3 specific antagonists, although they may improve these characteristics. The purpose for which the substitution is made is not important, and may include, but is by no means limited to, substituting a certain residue with a residue that can better maintain or enhance the molecular structure, the charge or hydrophobicity of the molecule, or the size of the molecule. For example, it may be desirable to substitute a less desirable residue with a residue having the same polarity or charge. Such modifications can be introduced using standard techniques known in the art such as site-directed mutagenesis and PCR-mediated mutagenesis. A specific way for those skilled in the art to achieve conservative amino acid substitutions is alanine scanning mutagenesis, as described in, for example, MacLennan et al., 1998 Acta Physiol. Scand. Suppl. 643: 55-67, and Sasaki et al., 1998 Adv. Biophys 0.35: 1-24. The functional tests available in the art or described herein are then used to test whether the modified antagonist retains function or has better function. The B7-H3 specific antagonist with the following characteristics is referred to herein as the "functional equivalent" of the antagonist disclosed herein and constitutes a specific embodiment of the present disclosure: having one or more of the conservative amino acid substitutions described herein, retaining the ability to selectively bind to human B7-H3, and to antagonize the function of B7-H3 at the same level or better than molecules without amino acid substitutions, as described above.

Generally, a B7-H3 specific antagonist having an amino acid sequence homologous to the amino acid sequence of the antagonist described herein is prepared to improve one or more properties of the antagonist without changing its specificity for B7-H3. One method of obtaining an antagonist with such sequences (not the only method available to those skilled in the art) is to mutate the sequence encoding the B7-H3 specific antagonist or its specificity determining regions, express the antagonist containing these mutant sequences, and use available functional assays (including those described herein) to detect whether these encoded antagonists retain functions. Mutation can be performed by site-directed mutagenesis or random mutagenesis. However, those skilled in the art will understand that other mutagenesis methods can easily achieve the same effect. For example, in some methods, the mutant spectrum is limited by non-random target conservative substitutions based on the chemical or structural properties of amino acids, or by considerations of protein structure. In an affinity maturation assay, several such mutations can be found in a single selected molecule (either randomly or non-randomly selected). For affinity maturation, there are various structure-based methods, which are described in, for example, U.S. Pat. No. 7,117,096, PCT Publication Nos. WO 02/084277 and WO03/099999.

The following examples further illustrate the present disclosure, but the present disclosure is not limited thereto. In the following examples, the experimental methods without specific conditions are selected according to conventional methods and conditions, or according to the commercial manual.

Example 1 Preparation of Human B7-H3 Protein

The selected nucleic acid sequence encoding amino acids 29-245 of human 2Ig B7-H3 was named H2M after the addition of a 10 His tag for purification at the N-terminus and a Myc tag for detection at the C-terminus; the selected nucleic acid sequence encoding amino acids 27-461 of human 4Ig B7-H3 was named H4M after the addition of a 10 His tag for purification at the N-terminus and a Myc tag for detection at the C-terminus; and the selected nucleic acid sequence of amino acids 27-461 of human 4Ig B7-H3 was named M4H after the addition of a Myc tag for detection at the N-terminus and a 10 His tag for purification at the C-terminus. The gene plasmids H2M-pUC57, M4H-pUC57 and H4M-pUC57 of the three B7-H3 antigens described above were synthesized respectively, and pv81 expression vector plasmids were synthesized. After digestion with EcoRI and SmaII and ligation, they were transformed into $E.$ $coli$ competent cells Trans-T1, then the clones validated by PCR screening and amplification were subjected to large scale extraction of plasmid. The extracted expression vectors H2M, H4M and M4H were respectively transiently transfected into Expi293 and expressed for 7 days, and the supernatant obtained from the expression was detected by ELISA and purified.

For biotinylated antigen preparation, the prepared H4M antigen (with a concentration of 3.36 mg/mL) was incubated with PBS and 10 µM biotin at 37° C. The ratio of the amount of the antigen to the biotin was 1:10. After incubating for 30 minutes, 0.1 mL of 3 M Tris was pipetted in to stop the reaction. The biotinylated antigen was concentrated and its buffer was replaced with 20 mM PB, 150 mM NaCl, pH 7.4 to remove free biotin. The final labeling amount of H4M antigen after biotin labeling was calculated to be approximately 2.5.

Example 2 Library Preparation 1 ml of bacteria broth containing library Lambda with a size of $2.91*10^9$ and 1 ml of bacteria containing library Kappa with a size of $3.72*10^9$ was added with 2.0 L of fresh medium 2YT containing 100 µg/ml Amp and 2% glucose, respectively. The starting OD600 of the bacteria broth containing the libraries describe above was less than 0.1 and it was incubated at 37° C. and 200 rpm. When OD600 reached 0.5-0.6, 365 µl of M13K07 was added with a titer of $9.6*10^{12}$/ml and the added amount is 10 times the amount of bacteria, and the amount of bacteria=OD600*$8.0*10^8$/ ml* bacterial volume cultured on a shaker, then helper phagemid infection was performed. The helper phage was added to the bacteria broth and incubated statically at 37° C. for 30 min, then incubated at 200 rpm for 30 min, and finally centrifuged at 4000 rpm for 10 min. The bacteria broth was resuspended with 2.0 L equal volume of 2YT containing 100 µg/ml Amp and 50 µg/ml Kana, and cultured at 30° C. for 16 h for expression. After the expression was finished, the bacteria broth was centrifuged at 8000 rpm for 30 minutes at 4° C., and the supernatant was removed. The supernatant was centrifuged at high speed to remove the bacteria, then 1/5 volume of PEG/NACL was added to precipitate phage in the supernatant. After centrifugation, the phage was dissolved in PBS. The phage titer was detected to be approximately $2.1*10^{11}$.

Example 3 Screening of Anti-B7-H3 Antibody Phage Library

Solution-phase panning: 150 µL of Dynabeads™ M-280 magnetic beads were blocked with 1% casein for 1 h at room temperature, then 100 µL of the prepared phage library was added, shaken gently, and blocked at room temperature for 1 h. After being blocked, 30 µg of biotinylated B7-H3 antigen H4M was added and incubated at room temperature for 1 hour. Then the complex of antigen H4M and anti-phage antibody was incubated with the blocked magnetic beads for 15 minutes to make the complex bind to the magnetic beads. After washed for 15 times with PBST and PBS respectively, 1 ml of trypsin (10 µg/ml) was added to elute the phage bound to the antigen, with an elution volume of 1 ml. The phage was infected with TG1 in the logarithmic phase, and the titer was measured, then the phage was amplified for the next round of panning. A total of 3 rounds of panning were performed. The process of the last two rounds of panning were the same as the first round, but the amount of biotinylated antigen H4M added was gradually reduced to 10 µg and 5 µg or 7.5 µg and 2.5 µg, respectively.

Phage ELISA screening: streptavidin with a concentration of 1 mg/ml was taken and dissolved at room temperature, after being mixed, it was diluted gradually with coating buffer to 5 µg/ml. 100 µL/well of which was then pipetted into each well in a 96-well plate, and 100 µL coating buffer only were pipetted into another 3 wells as a blank control, incubated overnight at 2-8° C. The biotinylated B7-H3 antigen H4M was taken and diluted with 0.5% BSA-PBST diluent to 50 ng/ml, then 100 µL of which at a concentration of 20 ng/ml was pipetted into the streptavidin-coated wells, and placed into a microplate shaker. After shaking at 37° C. and 600 rpm for 1 hour, the liquid was discarded, the plate was washed for 3 times with washing buffer and pat dry. The positive phage obtained in the second or third round of panning was taken and dissolved at room temperature, after being mixed, it was diluted 500 times with the diluent. The diluted phage was aliquoted into the microtiter plate at an amount of 100 µL/well, and placed in a microplate shaker, incubating at 37° C. and 600 rpm for 1 hour. After discarding the liquid, the plate was washed for 3 times with washing buffer. Then 100 µL of diluted HRP/Anti-M137 enzyme-linked antibody was aliquoted into each well, placed into the microplate shaker, incubating at 37° C., 600 rpm for 1 hour. After discarding the liquid, the plate was washed for 3 times. Then TMB chromogenic solution was aliquoted in at 100 µL/well and incubated for color development for 15 minutes, then 1 mol/L $H_2SO_4$ stop solution was aliquoted at 100

µL/well to stop the reaction. A microplate reader was used to measure the absorbance at 450 nm with a wavelength of 650 nm as the reference wavelength.

ELISA screening of scFv protein: B7-H3 antigen H4M was taken and dissolved at room temperature, then diluted with coating buffer to 2 ng/ml, and aliquoted into a hydrophobic enzyme-labeled plate at 100 µL/well, while 100 µL coating buffer only were pipetted into another 3 wells as a blank control, incubated overnight at 2-8° C. 100 µL of scfv protein sample was pipetted into each well, then the plate was placed into the microplate shaker, incubating for 1 hour at 37° C. and 600 rpm. After discarding the liquid, the plate was washed for 3 times with washing buffer. Then diluted enzyme-linked antibody was aliquoted into each well at 100 µL/well, placed into the microplate shaker, incubating at 37° C., 600 rpm for 1 hour. After discarding the liquid, the plate was washed for 3 times. Then TMB chromogenic solution was aliquoted in at 100 µL/well and incubated for 15 minutes, then 1 mol/L $H_2SO_4$ stop solution was aliquoted at 100 µL/well to stop the reaction. A microplate reader was used to measure the absorbance at 450 nm with a wavelength of 650 nm as the reference wavelength.

As described above, a total of 60 scFv antibodies against B7-H3 with unique sequences were screened. The sequences of the exemplary antibodies P1D1, P1G2, P2E5, P1E11, P2E3, P3B9, P3H6, P7F10 and P9A12 are shown in Table 1 wherein the CDRs are determined according the Kabat numbering scheme.

TABLE 1

| Antibody name | scFv (SEQ ID NO) | VH (SEQ ID NO) | Heavy chain CDR1 (SEQ ID NO) | Heavy chain CDR2 (SEQ ID NO) | Heavy chain CDR3 (SEQ ID NO) | VL (SEQ ID NO) | Light chain CDR1 (SEQ ID NO) | Light chain CDR2 (SEQ ID NO) | Light chain CDR3 (SEQ ID NO) |
|---|---|---|---|---|---|---|---|---|---|
| P1D1 | 5 | 6 | 7 | 8 | 9 | 10 | 11 | 12 | 13 |
| P2E5 | 14 | 15 | 16 | 17 | 18 | 19 | 20 | 21 | 22 |
| P1E11 | 23 | 24 | 25 | 26 | 27 | 28 | 29 | 30 | 31 |
| P1G2 | 32 | 33 | 34 | 35 | 36 | 37 | 38 | 39 | 40 |
| P3B9 | 41 | 42 | 7 | 8 | 43 | 44 | 45 | 12 | 46 |
| P2E3 | 47 | 48 | 7 | 8 | 49 | 50 | 51 | 52 | 53 |
| P3H6 | 70 | 71 | 72 | 8 | 74 | 75 | 76 | 77 | 78 |
| P7F10 | 79 | 80 | 81 | 82 | 83 | 84 | 85 | 86 | 87 |
| P9A12 | 88 | 89 | 90 | 91 | 92 | 93 | 94 | 95 | 96 |

The binding signal values of antibodies P1D1, P1G2, P2E5, P1E11, P2E3, P3B, P3H6, P7F10 and P9A129 with B7-H3 antigen H4M in phage ELISA and scFv protein ELISA are shown in Table 2 below. The results show that the scFv antibodies screened all showed better binding signal values for B7-H3 protein.

TABLE 2

ELISA signal value of Phage scFv and protein scFv binding to H4M

| Antibody name | Sequence | ELISA signal value of Phage scFv | ELISA signal value of protein scFv |
|---|---|---|---|
| P1D1 | SEQ ID NO: 5 | 3.65 | 2.97 |
| P2E5 | SEQ ID NO: 14 | 0.74 | 0.84 |
| P1E11 | SEQ ID NO: 23 | 0.92 | 0.20 |
| P1G2 | SEQ ID NO: 32 | 3.55 | 0.54 |
| P3B9 | SEQ ID NO: 41 | 3.09 | 3.39 |
| P2E3 | SEQ ID NO: 47 | 3.54 | 3.58 |
| P3H6 | SEQ ID NO: 70 | 3.05 | 0.79 |

TABLE 2-continued

ELISA signal value of Phage scFv and protein scFv binding to H4M

| Antibody name | Sequence | ELISA signal value of Phage scFv | ELISA signal value of protein scFv |
|---|---|---|---|
| P7F10 | SEQ ID NO: 79 | 0.65 | 0.96 |
| P9A12 | SEQ ID NO: 88 | 0.78 | 0.94 |

Example 4 ELISA Binding of Anti-B7-H3 Full-Length Antibody Protein

ELISA Binding of Anti-B7-H3 Full-Length Antibody Protein

Preparation of IgG1 antibody: scFv was converted into the form of IgG1. The VH domain and VL domain of scFv that the inventor wanted to convert into IgG molecule were cloned into a vector containing a nucleotide sequence encoding a suitable heavy chain (human IgG1) or light chain (human kappa or human lambda) constant region, so that intact heavy chain or light chain molecules could be expressed by the vector after being transfected into a suitable host cell. In addition, when the cloned heavy chain and light chain were expressed simultaneously in a cell line (from one vector or two vectors), they could be assembled into an intact functional antibody molecule, which was secreted into the cell culture. The conversion of scFv into conventional antibody molecule is a well-known technique in the art (the VH and VL of a scFv are directly assembled on the heavy chain constant region and the light chain constant region of a full-length antibody, respectively). 9 pairs of light and heavy chain primer sequences for the above exemplary antibodies such as P1G2, P1E11, P2E3, P2E5, P3B9, P1D1, P3H6, P7F10 and P9A12 were designed, except that the light chain of P1E11 was constructed into pfu-CLIg-hk (Invitrogen) vector by using EcoRI and BsiWI double enzyme digestion, the light chains of the rest antibodies were constructed into pfu-CLIg-h12 (invitrogen) vector by using EcoRI and ArvII double enzyme digestion, and the heavy chains were constructed into pfu-CLIg-Hg1 (invitrogen) vector by EcoRI+NheI double enzyme digestion H chain (IgG1). After target clones were validated by PCR screening and amplification, a large-scale extraction of plasmids was performed (see J. Sambrook. Molecular Cloning: A Laboratory Manual ($2^{nd}$ Edition) [M]. Science Press, 1992). The extracted expression vectors were transiently transfected into CHO—S cells and expressed for 7 days, and the supernatant obtained from the expression was detected by ELISA and purified.

Figure 7:
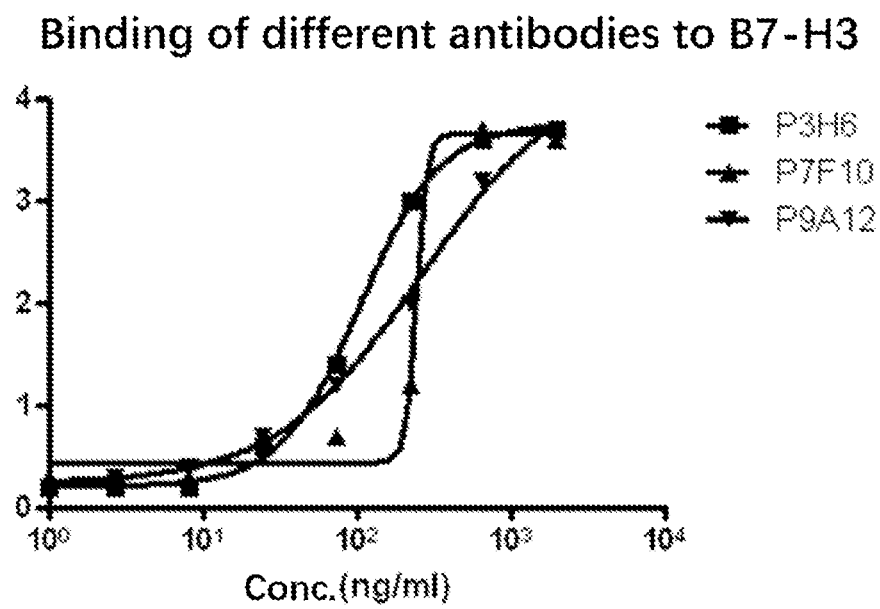
FIG. 7 shows the ELISA results of the binding of antibodies P9A12, P7F10 and P3H6 to B7-H3.

Protein binding: 100 μL of antigen B7-H3 (R&D) at 20 ng/ml was coated onto microplate, incubated at 2-8° C. overnight. Subsequently, 100 μL of the prepared full-length IgG1 antibody described above was added with a total of 8 concentrations started from 2000 ng/ml and serially diluted with 3-fold, incubating at 37° C., 600 rpm for 1 hour. After the plate was washed for three times, Goat anti human IgG (Fc)-HRP enzyme-linked antibody was added and the plate was shook at 37° C. and 600 rpm for 1 hour. After the plate was washed for 4 times, TMB chromogenic solution was aliquoted in and incubated for 10 minutes, then 1 mol/L H2SO4 stop solution at 100 μL/well was aliquoted to stop the reaction and the absorbance was measured. As a result, except that P1E11 and P2E3 do not bind to the coated B7-H3 protein, the other antibodies specifically bind to B7-H3 antigen, as shown in FIG. 1 and FIG. 7, antibodies such as P1D1, P3B9, P1G2, P2E5, P3H6, P7F10 and P9A12 can bind to B7-H3 protein.

Example 5 Cell-Based ELISA Binding Evaluation of Anti-B7-H3 Antibody

Figure 2:
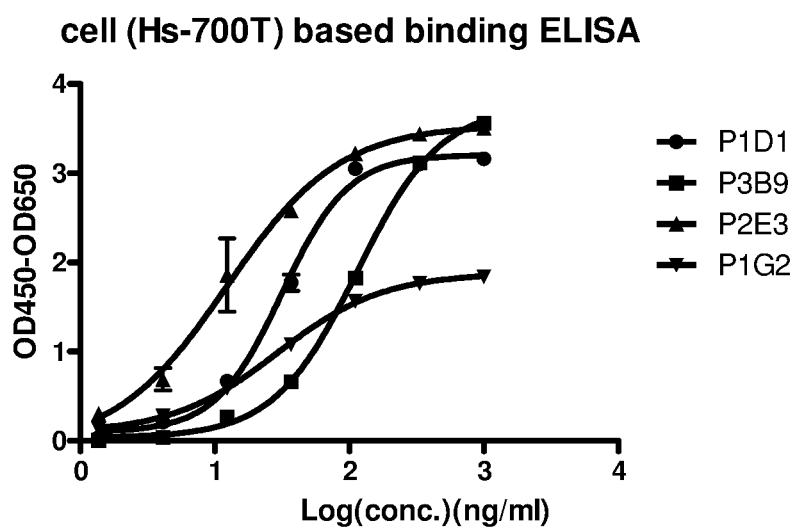
FIG. 2 shows the binding of antibodies P1G2, P1D1, P3B9 and P2E3 to Hs-700T cells.
Figure 8:
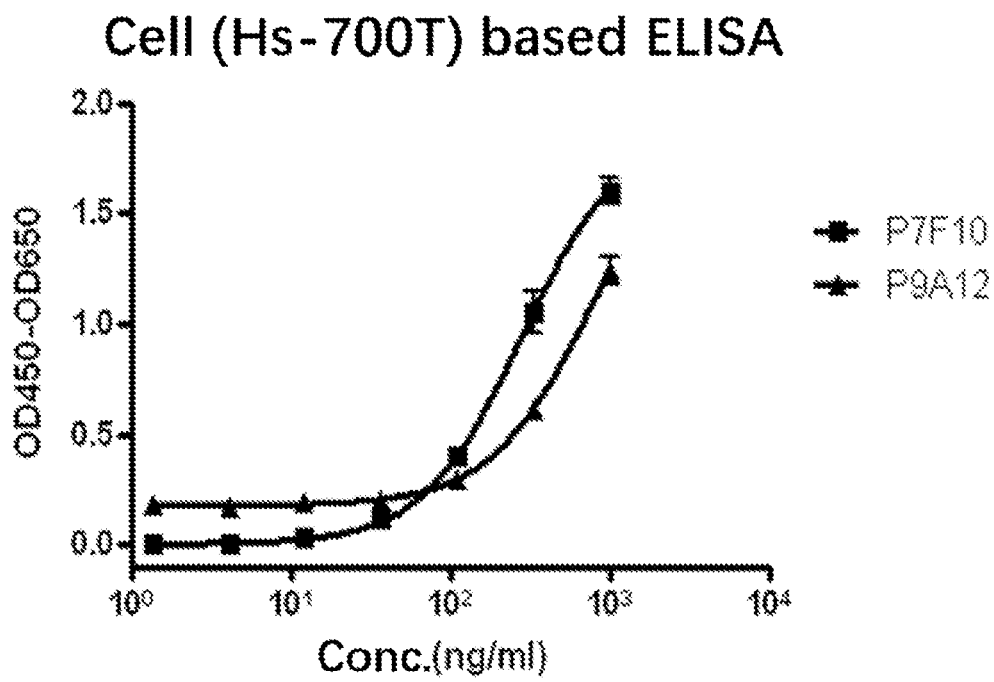
FIG. 8 shows the ELISA results of the binding of antibodies P9A12 and P7F10 to Hs-700T cells.

After the pancreatic cancer cell line Hs-700T was cultured, FBS/DMEM medium was added and then the cells were coated onto a plate at 20,000 cells/well. Wells without cells were added with complete cell culture medium as a blank control. The plate was then incubated at 37° C., 5% $CO_2$ for 20 to 24 hours. After the plate was washed once with PBST, 200 μl/well of formaldehyde was added for 0.5 hour at room temperature for fixing. After the plate was washed 3 times, 10% skimmed milk powder was added for 1 hour at room temperature for blocking, then the plate was washed for 3 times and pat dry. After the IgG1 antibodies prepared above such as P2E3, P1D1, P3B9, P3H6, P7F10 and P9A12 were mixed, respectively, each antibody was diluted with 0.5% BSA-PBST diluent to 10000 ng/ml, and then serially diluted to a total of 8 concentrations, and 100 μL/well of which were pipetted into the plate that had been coated with Hs-700T. The plate was incubated at room temperature for 1 hour, and then washed for 3 times. TMB chromogenic solution was then added to stop the reaction and the absorbance was measured. As a result, FIG. 2 and FIG. 8 show that antibodies P1D1, P1G2, P3B9, P2E3, P7F10 and P9A12 can bind to Hs-700T cells.

Figure 3:
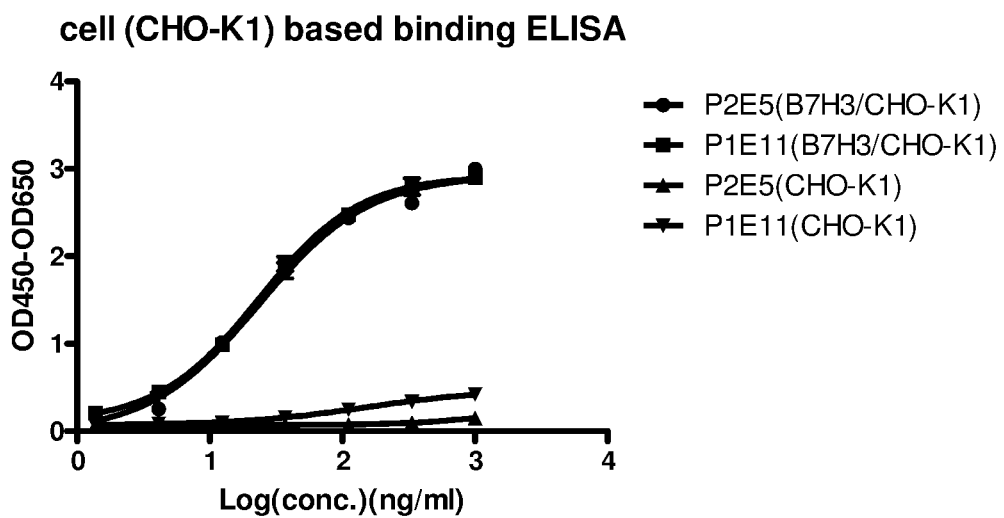
FIG. 3 shows the binding of P2E5 and P1E11 to B7-H3 transfected CHO cells.
Figure 9:
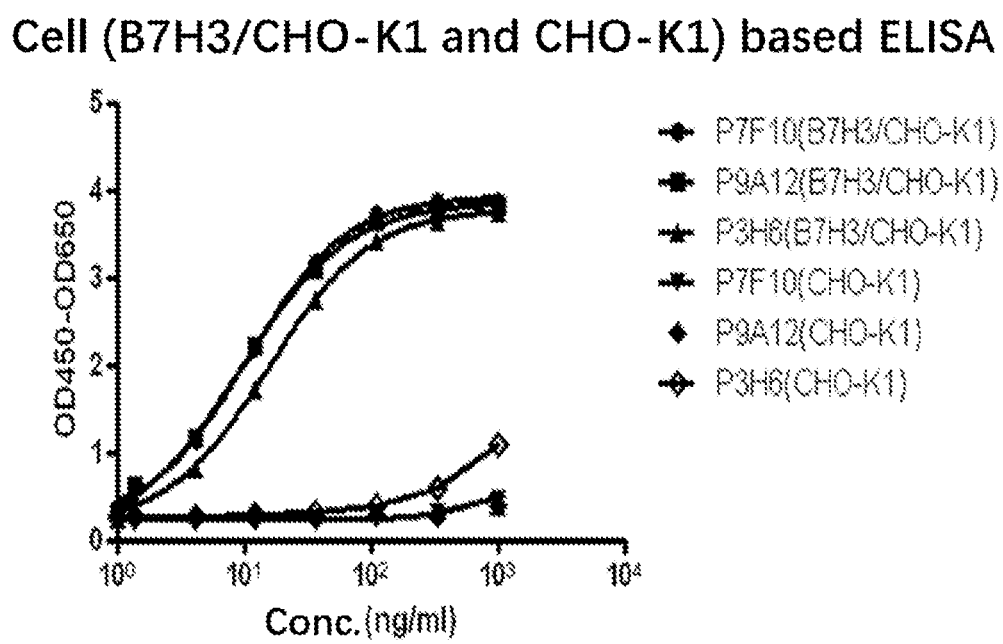
FIG. 9 shows the ELISA results of the binding of antibodies P9A12, P7F10 and P3H6 to CHO cells transfected with B7-H3.

Using the same method described above, it can be confirmed that the prepared IgG1 antibodies bind to B7-H3 transfected CHO cells. The results in FIG. 3 and FIG. 9 show that P2E5, P1E11, P9A12, P7F10 and P3H6 can bind to B7-H3 transfected CHO cells.

Another antibody, P1G2, specifically binds to the protein and Hs-700T cells and CHO cells. The binding level of this antibody is listed in the figures. The cell-level binding is not listed yet, but its cell-level binding activity is relatively weak, but its ADC activity is the best in the subsequent evaluation of ADC killing.

Example 6 Binding of Anti-B7-H3 Antibody to B7-H3 Domain

With the same protocols as in Example 4, the binding of IgG1 antibodies P1G2, P2E5, P1E11, P3H6, P7F10, and P9A12 to the 2IgB7-H3 domain, IgC domain, and IgV domain of B7-H3 were detected by ELISA. As a result, as shown in Table 3, it is confirmed that P1G2 binds to the IgC and IgV domains of B7-H3, P2E5 binds to the IgC domain of B7-H3 and weakly binds to the IgV domain of B7-H3, while P1E11 binds to the IgC domain of B7-H3 but not the IgV domain. These results show that P1G2 antibody binds to the IgC domain (SEQ ID NO: 56) and IgV domain (SEQ ID NO: 57) of B7-H3. In the same way, it is also confirmed that P2E5 binds to the IgC domain and weakly binds to the IgV domain, and P1E11 only binds to the IgC domain. P3H6 has a strong binding with the IgV domain (SEQ ID NO: 57), but does not bind to the IgC domain. P7F10 and P9A12 have certain binding with the IgC domain (SEQ ID NO: 56) and IgV domain (SEQ ID NO: 57).

TABLE 3

Binding of P1G2, P2E5 and P1E11 and P1G2, P2E5 and P1E11 to different domains of B7-H3

| Sample NO. | 4Ig B7-H3 | 2Ig B7-H3 | IgC Domain | Ig V Domain |
|---|---|---|---|---|
| P1E11 | ++++ | +++ | ++ | × |
| P1G2 | +++ | ++ | + | + |
| P2E5 | ++ | + | + | + |
| P3H6 | +++ | ++ | × | +++ |
| P7F10 | +++ | + | + | ++ |
| P9A12 | +++ | + | + | + |

Note:
+, weak binding; ++, medium level binding; +++, strong binding; ×, no binding; the binding level is determined based on the ELISA signal value, no binding: 0.1~0.2; weak binding: 0.3~0.5; medium level binding: 0.6~1.5; strong combination: 1.6~3.0.

Figure 4A:
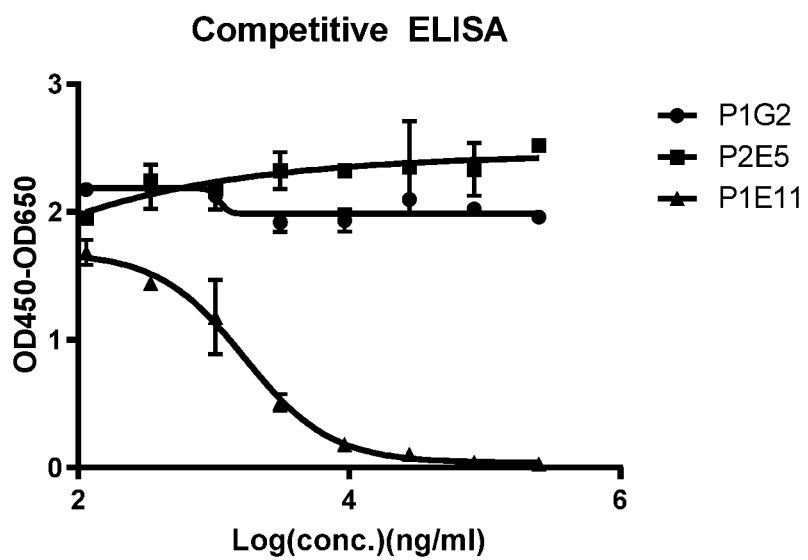
FIG. 4A shows that P1G2, P2E5, and P1E11 compete with biotin-P1E11 for binding to B7H3/4Ig.
Figure 4B:
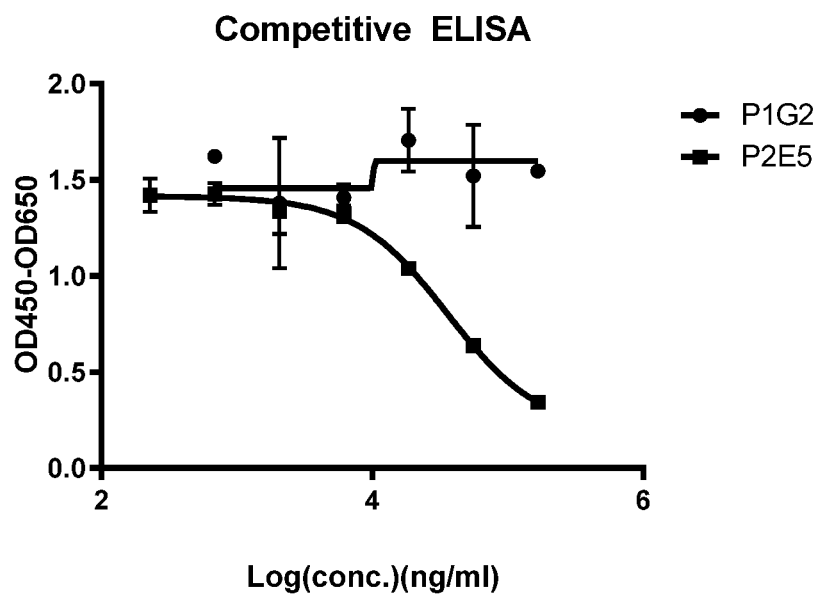
FIG. 4B shows that P1G2, P2E5 compete with biotin-P2E5 for binding to B7H3/4Ig.

The 4Ig-B7H3 antigen was fixed on an ELISA plate and used to bind to the biotin-labeled P1E11 antibody (biotin-labeled DAR-2.5), and the IgG1 antibody P1G2 and P2E5 with serially diluted concentrations were added to compete with P1E11 for the binding. The enzyme-linked secondary antibody was Streptavidin-HRP (1:400). Commercial chromogenic reagents and appropriate color development time were adopted, and the blank response value≤0.1 was a basic requirement. The results are shown in FIG. 4A, P1G2 and P2E5 do not compete with P1E11 for the binding, indicating that P1G2 and P2E5 bind different epitopes from P1E11. In the same way, P1G2 and P2E5 with serially diluted concentrations compete with the biotin-labeled P2E5 antibody (biotin-labeled DAR-2.0). As shown in FIG. 4B, it is also confirmed that the prepared antibody P1G2 does not compete with P2E5 to bind to B7-H3, indicating that P1G2 and P2E5 bind to different epitopes of B7-H3, respectively. Therefore, the prepared P1G2, P2E5 and P1E11 bind different epitopes of B7-H3, respectively.

Example 7 Internalization of Anti-B7-H3 Antibody after Binding to B7-H3

Figure 5:
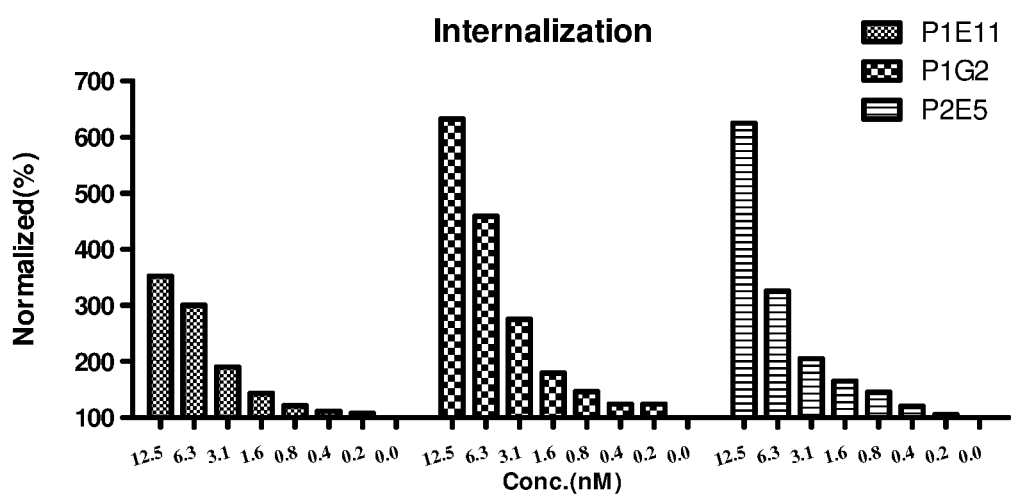
FIG. 5 shows that different anti-B7-H3 antibodies are internalized upon binding to tumor cell lines.
Figure 10:
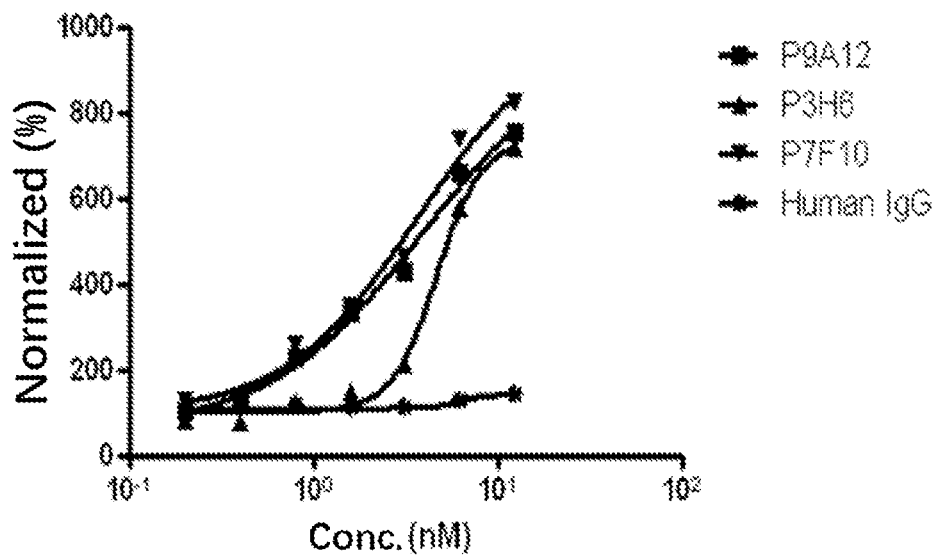
FIG. 10 shows that antibodies P9A12, P7F10 and P3H6 are internalized upon binding to tumor cell lines.

The ability of the anti-B7-H3 antibodies of the present disclosure to be internalized after binding to cancer cells was investigated. Pancreatic cell carcinoma Hs700T (purchased from ATCC) was inoculated into a 96-well cell culture plate at 80,000 cells/50 μl per well, culturing for 20-24 hr; subsequently, the anti-B7-H3 antibodies of the present disclosure such as P1G2, P2E5, P1E11, P1G2, P2E5 and P1E11 were diluted to 12.5, 6.3, 3.1, 1.6, 0.8, 0.4, 0.2 nM and 0 nM with cell medium containing 15% FBS corresponding to the cells to prepare diluted anti-B7-H3 antibodies with 8 concentrations, respectively, then were mixed with 200 nM (30 μg/ml) of PA-Goat anti-Human IgG Fc Antibody (DAR-10.6) at a 1:1 equal volume and directly transferred to a culture plate inoculated with cells at 50 μl/well, mixed gently for 1-2 minutes, incubating at 37° C. for internalization reaction for 24 hr. Then the plate was taken out and the culture solution was discarded, 100 μl of 1×PBS (pH8.0) was added and the bottom reading mode for reading the plate was selected with an excitation wavelength of 532 nm and an emission wavelength of 560 nm. The results shown in FIG. 5 and FIG. 10 indicate that the anti-B7-H3 antibodies of the present disclosure have the ability to be internalized or has a strong internalization activity within 24 hours after binding to cancer cells.

Example 8 ADC Killing Evaluation (i) Preparation of Conjugates of DM1 ADC Samples Appropriate amount of antibody samples P1G12, P2E5 and P1E11 were taken respectively, and replaced in a buffer solution system of 50-mM potassium phosphate, 50-mM NaCl, 1-mM HEPES (4-(2-hydroxyethyl)-1-piperazineethanesulfonic acid), pH 7.4, and the concentration was controlled at about 10 mg/mL. The antibody samples described above were then placed in a reactor, SMCC (the molar ratio of antibody to SMCC is 1:7.5) was added under stirring, and the reaction was performed at room temperature for 2 hours. The obtained samples were replaced with a buffer system of 50-mM sodium phosphate, 100-mM NaCl, 60-mM sodium octanoate, pH 7.5, and then placed in the reactor. The DM1 drug (the molar ratio of antibody to DM1 is 1:5) dissolved in DMA was added under stirring and the reaction was performed at room temperature for 1 hour. After the reaction, the prepared DM1 ADC samples were taken out and replaced with a buffer system of 10-mM citric acid, 60-g/L sucrose, pH 5.0. After the preparation, the DAR values of the prepared ADC samples were analyzed by mass spectrometry.

Lung cancer cell line NCI-H322 (which was purchased from Nanjing cobioer Biotechnology Co., Ltd.) was incubated with the anti-B7-H3 antibody conjugated drugs P1G2-DM1, P2E5-DM1, and P1E11-DM1 prepared by coupling with MCC-DM1. By measuring the cell viability, the internalization and killing activity of the DM1 ADC (DAR 3.2-3.5) of the anti-B7-H3 antibody of the present disclosure on tumor cells were evaluated.

Figure 6:
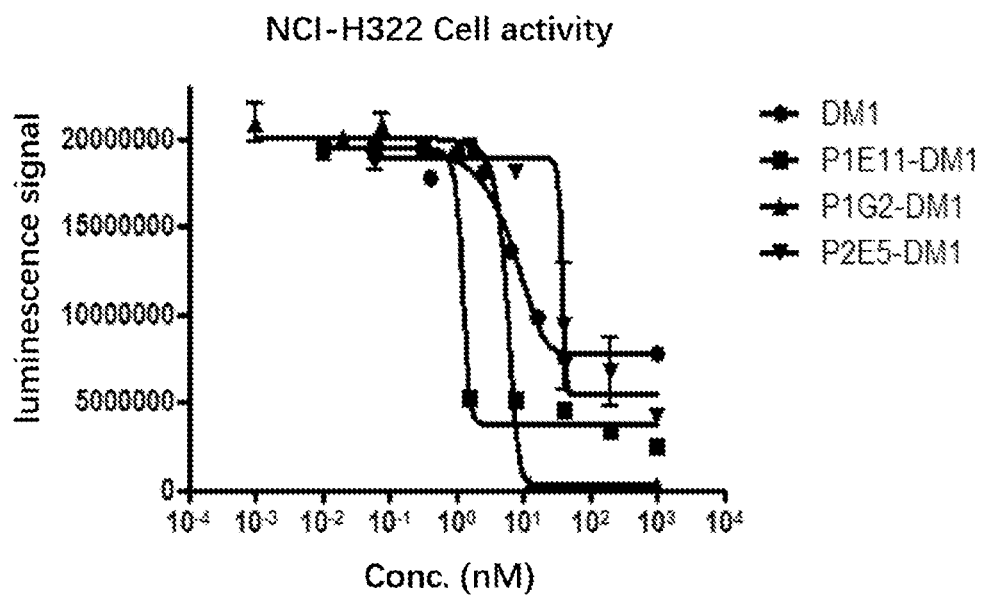
FIG. 6 shows the killing activity of DM1 ADCs of anti-B7-H3 antibody.

The results in FIG. 6 also show that the anti-B7-H3 antibody-conjugated drugs P1G2-DM1, P2E5-DM1 and P1E11-DM1 of the present disclosure all exhibit good ADC internalization and killing activity on tumor cells.

(ii) Preparation of Conjugates of MMAE ADC Samples

Appropriate amount of antibody samples P3H6, P7F10 and P9A12 were taken, respectively, and diluted with a buffer of 50 mM PB, 1 mM EDTA, pH 7.4 at a volume ratio of 1:1, and the pH was adjusted to 7.4 with buffer 3M Tris to control the sample concentration at about 5 mg/mL. Then the samples were placed in a reactor for reduction with a temperature of 37° C. and a stirring speed of 600 rpm. After preheated for 5-10 minutes, the samples were quickly added into 1 mg/ml of TCEP solution, then the reactor was sealed with a Parafilm to react for 2 hours. After the reduction reaction was over, the sample was immediately transferred to another reactor with a temperature of 0-6° C., stirring at 600 rpm in the open state, the VC-PAB-MMAE solution was slowly added to react for 40 minutes, and the samples were taken at the end of the reaction. The samples were replaced in a buffer solution of 50-mM PB, 1-mM EDTA, pH 6.0, the fluid exchange times for TFF were up to 15CV; ultrafiltration concentration tube up to 200 times the volume ratio. After changing the solution, 1/6 of the total sample volume of 42% sucrose was added to store for later use.

Lung cancer cell line Calu-6 (ATCC) was incubated with the anti-B7-H3 antibody conjugated drugs P3H6-MMAE, P7F10-MMAE and P9A12-MMAE prepared by VC-PAB-MMAE coupling. By measuring cell viability, the internalization and killing activity of the MMAE ADC (DAR 4.0±0.2 or so) of the anti-B7-H3 antibody of the present disclosure on tumor cells were evaluated.

Figure 11:
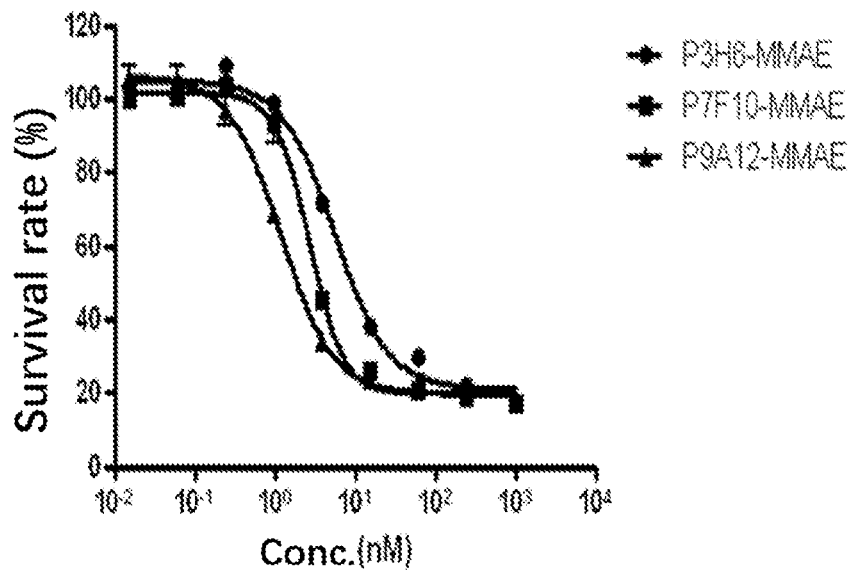
FIG. 11 shows the killing activity of MMAE ADCs of antibodies P9A12, P7F10 and P3H6 against Calu-6.

The results shown in FIG. 11 indicate that the anti-B7-H3 antibody conjugated drugs P3H6-MMAE, P7F10-MMAE and P9A12-MMAE of the present disclosure all show good ADC killing activity on the tumor cell calu-6.

Example 9 Evaluation of the Kinetics of Antibody's Interaction with B7-H3 Using Surface Plasmon Resonance ("SPR")

SPR detection was performed with BIAcore T200 (GE) system. Series Sensor Chip CM5 and the amine coupling kit for immobilization were purchased from GE.

Samples of antibodies P1G2, P2E5, P1E11, P3H6, P7F10, and P9A12 were diluted to 10 µg/ml with pH 5.5 NaAc buffer, the flow rate was set to 10 µL/min, and the the chip was activated by the mixture of EDC and NHS for the default time of 420 s, the antibody samples described above were fixed respectively using the preset coupling amount mode at a level of 200 RU, and the unbound activated group of the samples were blocked with ethanolamine.

The B7-H3 antigen was diluted with HBS-EP buffer in a certain proportion to concentration gradients of 0 nM, 0.15625 nM, 0.3125 nM, 0.625 nM, 1.25 nM (two replicates), 2.5 nM, 5 nM, 10 nM, 20 nM, the flow rate was set to 30 µL/min, the binding time was set to 120 s, and the dissociation time was set to 1800 s for sample analysis. For regeneration, Gly-HCl buffer (pH 1.5) could be used as a regeneration buffer, the flow rate was set to 30 µL/min, and regeneration was performed for 30 s. The experiment adopted multi-cycle operation, for the response signal, the analysis time was set as the abscissa and the response value was set as the ordinate. The obtained data was fitted by BIAcore T200 analysis software. The fitting model used was 1:1 Langmuir binding model, and the kinetic constants such as the binding rate constant, the dissociation rate constant, and the binding and dissociation constant were determined.

TABLE 4

Binding kinetic parameters of anti-B7-H3 antibodies

| Antibody name | Antigen | ka (1/Ms) | kd (1/s) | KD (M) |
|---|---|---|---|---|
| P1E11 | 4IgB7-H3 | 3.133E+6 | 7.763E−5 | 2.478E−11 |
| P1G2 | 4IgB7-H3 | 7.264E+6 | 1.670E−3 | 2.299E−10 |
| P2E5 | 4IgB7-H3 | 4.25E+4 | 5.90E−5 | 2.40E−9 |
| P3H6 | 4IgB7-H3 | 2.559E+5 | 6.649E−2 | 3.770E−7 |
| P7F10 | 4IgB7-H3 | 8.766E+5 | 2.485E−2 | 2.834E−8 |
| P9A12 | 4IgB7-H3 | 1.138E+6 | 1.97E−2 | 1.730E−8 |

What is claimed is:

1. An anti-B7-H3 antibody comprising the following complementarity determining regions: heavy chain CDR1, heavy chain CDR2, and heavy chain CDR3, and light chain CDR1, light chain CDR2, and light chain CDR3; wherein the heavy chain CDR1 comprises the amino acid sequence of SEQ ID NO: 34;

the heavy chain CDR2 comprises the amino acid sequence of SEQ ID NO: 35;

the heavy chain CDR3 comprises the amino acid sequence of SEQ ID NO: 36;

the light chain CDR1 comprises the amino acid sequence of SEQ ID NO: 38;

the light chain CDR2 comprises the amino acid sequence of SEQ ID NO: 39; and the light chain CDR3 comprises the amino acid sequence of SEQ ID NO: 40.

2. The anti-B7-H3 antibody of claim 1 comprising a heavy chain variable region and a light chain variable region; wherein the heavy chain variable region comprises the amino acid sequence of SEQ ID NO: 33, or an amino acid sequence having at least 90% homology with the amino acid sequence of SEQ ID NO: 33;

and the light chain variable region comprises the amino acid sequence of SEQ ID NO: 37, or an amino acid sequence having at least 90% homology with the amino acid sequence of SEQ ID NO: 37.

3. The anti-B7-H3 antibody of claim 1, wherein the antibody is in the form of any of the following antibodies:
(a) an intact immunoglobulin molecule;
(b) a scFv;
(c) a fusion protein containing scFv;
(d) a Fab fragment;
(e) a Fab' fragment;
(f) a F(ab)$_2$;
or, the antibody is a monoclonal antibody or a polyclonal antibody;
or, the antibody is a diabody.

4. The anti-B7-H3 antibody of claim 3, wherein the anti-B7-H3 antibody further comprises a heavy chain constant region of an antibody and a light chain constant region of an antibody.

5. The anti-B7-H3 antibody of claim 3, wherein the scFv comprises the amino acid sequence of SEQ ID NO: 32.

6. The anti-B7-H3 antibody of claim 1, wherein the B7-H3 is B7-H3 endogenously expressed on the surface of cancer cells.

7. The anti-B7-H3 antibody of claim 1, wherein the anti-B7-H3 antibody has a dissociation constant (KD) of $10^{-9}$ M or less.

8. A nucleic acid encoding the anti-B7-H3 antibody of claim 1.

9. A recombinant expression vector comprising the nucleic acid of claim 8.

10. A transformant comprising the recombinant expression vector of claim 9, wherein the transformant is an isolated host cell.

11. A method for the preparation of an anti-B7-H3 antibody comprising the following steps: culturing the transformant of claim 10, and harvesting anti-B7-H3 antibody from the culture.

12. An immunoconjugate comprising the anti-B7-H3 antibody of claim 1.

13. A pharmaceutical composition comprising the immunoconjugate of claim 12 and a pharmaceutically acceptable carrier.

14. A method for treating a disease associated with abnormal expression of B7-H3 in a subject in need thereof, comprising: administering an effective amount of the anti-B7-H3 antibody of claim 1, an immunoconjugate or a pharmaceutical composition;
wherein the disease associated with abnormal expression is a tumor;
the immunoconjugate comprises the anti-B7-H3 antibody of claim 1; and
the pharmaceutical composition comprises the immunoconjugate and a pharmaceutically acceptable carrier.

15. A transformant having the nucleic acid of claim 8 integrated into its genome, wherein the transformant is an isolated host cell.

16. The anti-B7-H3 antibody of claim 4, wherein the heavy chain constant region of antibody is a heavy chain constant region of human or mouse antibody, and the light chain constant region of antibody is a light chain constant region of human or mouse antibody.

17. The anti-B7-H3 antibody of claim 16, wherein the light chain constant region of human antibody is a kappa or lambda light chain constant region of human antibody, and the heavy chain constant region is human IgG1, IgG2, IgG3, or IgG4.

18. The anti-B7-H3 antibody of claim 16, wherein the amino acid sequence of the heavy chain of the anti-B7-H3 antibody comprises the amino acid sequence of SEQ ID NO: 58, or an amino acid sequence having at least 90% homology with the amino acid sequence of SEQ ID NO: 58;
and the amino acid sequence of the light chain of the anti-B7-H3 antibody comprises the amino acid sequence of SEQ ID NO: 59, or an amino acid sequence having least 90% homology with the amino acid sequence of SEQ ID NO: 59.

19. The anti-B7-H3 antibody of claim 3, wherein the monoclonal antibody is a fully human monoclonal antibody.

20. The anti-B7-H3 antibody of claim 6, wherein the anti-B7-H3 antibody is internalized upon binding to the B7-H3 endogenously expressed on the surface of cancer cells.

21. A transformant comprising the recombinant expression vector of claim 11, wherein the transformant is a CHO-S cell.

22. The immunoconjugate of claim 12, wherein the immunoconjugate is an antibody-drug conjugate.

23. The immunoconjugate of claim 22, wherein the anti-B7-H3 antibody is connected through a linker with a cytotoxic agent in the antibody-drug conjugate.

24. The immunoconjugate of claim 23, wherein the immunoconjugate meets one or both of the following:
the linker is SMCC or VC-PAB; and
the cytotoxic agent is MMAE or maytansine, and the antibody-drug ratio of the anti-B7-H3 antibody to the maytansine is 3.2-4.0.

25. The method of claim 14, wherein the method meets one or both of the following:
the tumor is a cancer; and,
the immunoconjugate is an antibody-drug conjugate.

26. The method of claim 25, wherein the method meets one or both of the following:
the cancer is lung cancer, breast cancer, prostate cancer, pancreatic cancer, colorectal cancer, melanoma, liver cancer, ovarian cancer, bladder cancer, stomach cancer, esophageal cancer, or kidney cancer; and,
the anti-B7-H3 antibody is connected through a linker with a cytotoxic agent in the antibody-drug conjugate.

27. The method of claim 26, wherein the immunoconjugate meets one or both of the following:
the linker is SMCC or VC-PAB; and
the cytotoxic agent is MMAE or maytansine, and the antibody-drug ratio of the anti-B7-H3 antibody to the maytansine is 3.2-4.0.

28. A transformant having the nucleic acid of claim 8 integrated into its genome, wherein the host of the transformant is a CHO-S cell.

* * * * *